US012599359B2

(12) United States Patent
Matsumoto

(10) Patent No.: US 12,599,359 B2
(45) Date of Patent: Apr. 14, 2026

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 6 days.

(21) Appl. No.: 17/589,076

(22) Filed: Jan. 31, 2022

(65) Prior Publication Data

US 2022/0175344 A1 Jun. 9, 2022

Related U.S. Application Data

(63) Continuation of application No. PCT/JP2020/026705, filed on Jul. 8, 2020.

(30) Foreign Application Priority Data

Aug. 19, 2019 (JP) ................................. 2019-149751

(51) Int. Cl.
*A61B 8/08* (2006.01)
*A61B 8/00* (2006.01)

(52) U.S. Cl.
CPC .......... *A61B 8/0891* (2013.01); *A61B 8/0841* (2013.01); *A61B 8/4494* (2013.01); (Continued)

(58) Field of Classification Search
CPC ... A61B 8/0891; A61B 8/0841; A61B 8/4494; A61B 8/461; A61B 8/469; A61B 8/54; (Continued)

(56) References Cited

U.S. PATENT DOCUMENTS

2010/0135562 A1 6/2010 Greenberg et al.
2012/0063661 A1* 3/2012 Nishimura ............. A61B 8/467
382/131
(Continued)

FOREIGN PATENT DOCUMENTS

JP 2002-085354 A 3/2002
JP 2014-054398 A 3/2014
(Continued)

OTHER PUBLICATIONS

The extended European search report issued by the European Patent Office on Sep. 13, 2022, which corresponds to European Patent Application No. 20854208.4-1126 and is related to U.S. Appl. No. 17/589,076.
(Continued)

*Primary Examiner* — Kaitlyn E Sebastian
(74) *Attorney, Agent, or Firm* — Studebaker Brackett PLLC

(57) ABSTRACT

Provided are an ultrasound diagnostic apparatus capable of appropriately displaying a measurement result regarding a target blood vessel in an ultrasound image within a display range of the ultrasound image, and a method of controlling the same.

An ultrasound diagnostic apparatus 1 includes a transducer array 2, an image acquisition unit 11 that acquires an ultrasound image, a display device 8 that displays the ultrasound image, a blood vessel information acquisition unit 16 that acquires blood vessel information including at least one of a diameter or a depth of a target blood vessel in the ultrasound image by analyzing the ultrasound image, a blood vessel information display unit 17 that displays the blood vessel information within a display range of the ultrasound image, a region-of-interest detection unit 18 that detects a region of interest in the ultrasound image to be noticed other than the target blood vessel by analyzing the (Continued)

ultrasound image, and an apparatus controller 13 that, in a case where the region of interest is detected, decides a display region of the blood vessel information in the display range based on a position of the region of interest and performs control such that the blood vessel information display unit 17 displays the blood vessel information in the display region.

20 Claims, 18 Drawing Sheets

(52) U.S. Cl.
CPC .............. *A61B 8/461* (2013.01); *A61B 8/469* (2013.01); *A61B 8/54* (2013.01); *A61B 8/565* (2013.01)

(58) Field of Classification Search
CPC ......... A61B 8/565; A61B 8/085; A61B 8/463; A61B 8/468; A61B 8/5223; A61B 8/12; A61B 8/14; A61B 8/52; A61B 8/5207; A61B 8/5215; A61B 8/523; G16H 30/40; G16H 40/63
See application file for complete search history.

(56) References Cited

U.S. PATENT DOCUMENTS

| | | | | |
|---|---|---|---|---|
| 2013/0225984 | A1* | 8/2013 | Cheng | G06T 19/00 |
| | | | | 600/424 |
| 2014/0037167 | A1* | 2/2014 | Shirahata | A61B 5/748 |
| | | | | 382/128 |
| 2015/0187119 | A1 | 7/2015 | Masumoto | |
| 2015/0220240 | A1 | 8/2015 | Tsukijishin et al. | |
| 2015/0351718 | A1* | 12/2015 | Vollmer | A61B 8/0808 |
| | | | | 600/437 |
| 2016/0157802 | A1* | 6/2016 | Anderson | A61B 8/12 |
| | | | | 600/407 |
| 2016/0278869 | A1* | 9/2016 | Grunwald | A61B 8/4472 |
| 2017/0128037 | A1* | 5/2017 | Mori | A61B 6/502 |
| 2017/0252006 | A1* | 9/2017 | Tsuruno | A61B 8/4461 |
| 2018/0000511 | A1* | 1/2018 | Fujie | A61B 8/54 |
| 2018/0014810 | A1* | 1/2018 | Chen | A61B 8/5246 |
| 2019/0128730 | A1* | 5/2019 | Stuart | G01H 3/125 |
| 2019/0216429 | A1* | 7/2019 | Sakai | A61B 8/4461 |

FOREIGN PATENT DOCUMENTS

| | | | | |
|---|---|---|---|---|
| JP | 2017-086561 | A | 5/2017 | |
| JP | 2017-524455 | A | 8/2017 | |
| WO | 2011/013346 | A1 | 2/2011 | |
| WO | WO-2019116592 | A1 * | 6/2019 | ......... A61B 1/00006 |

OTHER PUBLICATIONS

An Office Action; "Notice of Reasons for Refusal," mailed by the Japanese Patent Office on Oct. 18, 2022, which corresponds to Japanese Patent Application No. 2021-540659 and is related to U.S. Appl. No. 17/589,076; with English language translation.

International Search Report issued in PCT/JP2020/026705; mailed Oct. 6, 2020.

International Preliminary Report on Patentability and Written Opinion issued in PCT/JP2020/026705; issued Feb. 17, 2022.

Csurka et al.: Visual Categorization with Bags of Keypoints, Proc. of ECCV Workshop on Statistical Learning in Computer Vision, pp. 1-16, (2004).

Krizhevsky et al.: ImageNet Classification with Deep Convolutional Neural Networks, Advances in Neural Information Processing Systems 25, pp. 1-9, (2012).

* cited by examiner

FIG. 7

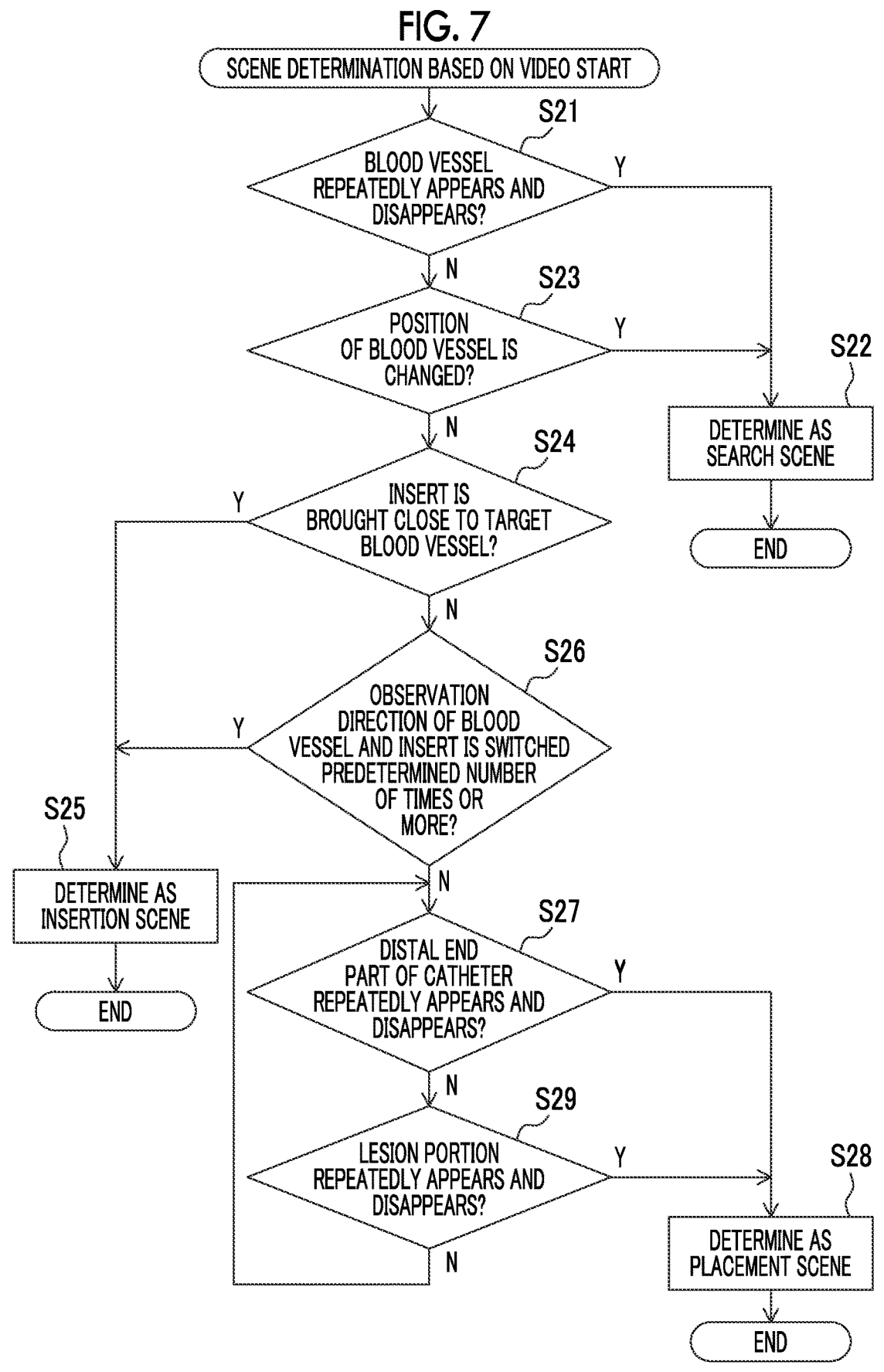

( SCENE DETERMINATION BASED ON VIDEO START )

S21

◇ BLOOD VESSEL REPEATEDLY APPEARS AND DISAPPEARS? ◇ —Y→

N

S23

◇ POSITION OF BLOOD VESSEL IS CHANGED? ◇ —Y→

S22

[ DETERMINE AS SEARCH SCENE ]

( END )

N

S24

Y←◇ INSERT IS BROUGHT CLOSE TO TARGET BLOOD VESSEL? ◇

N

S26

Y←◇ OBSERVATION DIRECTION OF BLOOD VESSEL AND INSERT IS SWITCHED PREDETERMINED NUMBER OF TIMES OR MORE? ◇

S25

[ DETERMINE AS INSERTION SCENE ]

( END )

N

S27

◇ DISTAL END PART OF CATHETER REPEATEDLY APPEARS AND DISAPPEARS? ◇ —Y→

N

S29

◇ LESION PORTION REPEATEDLY APPEARS AND DISAPPEARS? ◇ —Y→

S28

[ DETERMINE AS PLACEMENT SCENE ]

N ( END )

ELAPSED TIME

ELAPSED
TIME

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2020/026705 filed on Jul. 8, 2020, which claims priority under 35 U.S.C. § 119(a) to Japanese Patent Application No. 2019-149751 filed on Aug. 19, 2019. The above application is hereby expressly incorporated by reference, in its entirety, into the present application.

BACKGROUND OF THE INVENTION

1. Field of the Invention

The present invention relates to an ultrasound diagnostic apparatus that displays a blood vessel of a subject in an ultrasound image, and a method of controlling an ultrasound diagnostic apparatus.

2. Description of the Related Art

Hitherto, as an apparatus that obtains an image of the inside of a subject, an ultrasound diagnostic apparatus is known. In general, the ultrasound diagnostic apparatus has an ultrasound probe comprising a transducer array in which a plurality of ultrasound transducers are arranged. The ultrasound probe transmits an ultrasound beam from the transducer array toward the inside of the subject in a state of being brought into contact with a body surface of the subject and receives an ultrasound echo from the subject in the transducer array. With this, an electric signal corresponding to the ultrasound echo is acquired. The ultrasound diagnostic apparatus processes the acquired electric signal to generate an ultrasound image regarding a target part of the subject.

Incidentally, there is known a procedure for inserting an insert, such as a puncture needle and a catheter, into a blood vessel of a subject while observing the inside of the subject using the above-described ultrasound diagnostic apparatus, specifically, an echo guided puncture method. In the echo guided puncture method, usually, an operator confirms an ultrasound image to recognize the position, shape, and the like of a blood vessel in the ultrasound image, and then, decides a blood vessel into which the insert is to be inserted. In this case, a given level or higher of skill is required to accurately recognize the position, shape, and the like of the blood vessel. In a case where the operator searches for an appropriate blood vessel while imaging an ultrasound image in a video mode, interrupts imaging in the video mode when the blood vessel is rendered in the ultrasound image, switches the ultrasound image to a static image, and analyzes the static image to measure the diameter, the area, and the like of the blood vessel, the operation becomes complicated.

To solve the above-described problem, an ultrasound diagnostic apparatus that automatically detects a blood vessel included in an ultrasound image, measures the diameter and the area of the detected blood vessel, and displays a measurement result on a display screen has been hitherto developed. Examples of such an apparatus include an ultrasound diagnostic apparatus described in JP2017-524455A. With the apparatus, while ultrasound images are continuously acquired at a given frame rate, a feature quantity (for example, a diameter and the like) of a blood vessel in the ultrasound image is measured and the measurement result is displayed within a display range of the ultrasound image in real time.

SUMMARY OF THE INVENTION

It should be noted that, like the ultrasound diagnostic apparatus described in JP2017-524455A, in a case where information regarding a measurement result of a target blood vessel a diameter and the like of which are measured is displayed within the display range of the ultrasound image, and in a case where information is displayed near the target blood vessel, information is likely to overlap a target to be noticed (for example, another blood vessel that is present near the target blood vessel). In this case, a region to be noticed other than the target blood vessel cannot be confirmed in the ultrasound image, and there is a concern that an operation of the operator while viewing the ultrasound image is obstructed.

The present invention has been accomplished in view of the above-described situation, and aims to achieve the following objects.

An object of the present invention is to solve the problems in the related art described above and to provide an ultrasound diagnostic apparatus capable of appropriately displaying a measurement result regarding a target blood vessel in an ultrasound image within a display range of the ultrasound image and a method of controlling the same.

To achieve the above-described object, the present invention provides an ultrasound diagnostic apparatus that displays a blood vessel of a subject in an ultrasound image, the ultrasound diagnostic apparatus comprising a transducer array, an image acquisition unit that causes the transducer array to transmit an ultrasound beam toward the subject and receives an ultrasound echo by the subject to acquire an ultrasound image, a display device that displays the ultrasound image acquired by the image acquisition unit, a blood vessel information acquisition unit that detects a target blood vessel in the ultrasound image by analyzing the ultrasound image acquired by the image acquisition unit and acquires blood vessel information including at least one of a diameter or a depth of the detected target blood vessel, a blood vessel information display unit that displays the blood vessel information acquired by the blood vessel information acquisition unit within a display range of the ultrasound image in the display device, a region-of-interest detection unit that detects a region of interest in the ultrasound image to be noticed other than the target blood vessel by analyzing the ultrasound image acquired by the image acquisition unit, and an apparatus controller that, in a case where the region of interest is detected by the region-of-interest detection unit, decides a display region of the blood vessel information in the display range based on a position of the region of interest and performs control such that the blood vessel information display unit displays the blood vessel information in the decided display region.

In the ultrasound diagnostic apparatus of the present invention described above, the apparatus controller may extract a display candidate region avoiding the target blood vessel and the region of interest within the display range and may decide the display region from the extracted display candidate region.

In this case, it is more preferable that the apparatus controller decides the display region such that at least a part of the blood vessel information overlaps the region of interest in a case where the display candidate region is not extracted within the display range.

It is still more preferable that, in a case where the region-of-interest detection unit detects a plurality of the regions of interest, the apparatus controller sets priority to each of the plurality of the regions of interest and decides the display region such that at least a part of the blood vessel information overlaps the region of interest with the lower priority in a case where the display candidate region is not extracted within the display range.

It is still more preferable that the apparatus controller sets the priority of each of the plurality of the regions of interest based on the position of each of the plurality of the regions of interest in the display range.

The ultrasound diagnostic apparatus of the present invention described above may further comprise a scene determination unit that determines a scene in a case where the ultrasound image is acquired, by analyzing the ultrasound image acquired by the image acquisition unit. In this case, it is more preferable that the region-of-interest detection unit detects the region of interest corresponding to the scene determined by the scene determination unit.

In the above-described configuration, in a case where the scene determined by the scene determination unit is a search scene where the target blood vessel is searched, the region-of-interest detection unit may detect a lesion portion inside the subject or a blood vessel other than the target blood vessel as the region of interest.

In this case, a blood vessel into which an insert puncturing the subject is inserted, among blood vessels of the subject may correspond to the target blood vessel, and the scene determination unit may determine that the scene is the search scene in a case where the blood vessel of the subject is detected in the ultrasound image and the insert is not detected by analyzing the ultrasound image acquired by the image acquisition unit.

Alternatively, the image acquisition unit may continuously acquire the ultrasound images at a given frame rate, and the scene determination unit may analyze the ultrasound images of a plurality of frames continuously acquired by the image acquisition unit and may determine that the scene is the search scene in a case where appearance and disappearance of the blood vessel are repeated in the ultrasound images of the plurality of frames and in a case where a position of the blood vessel is changed in the ultrasound images of the plurality of frames.

In the above-described configuration, a blood vessel into which an insert puncturing the subject is inserted, among blood vessels of the subject may correspond to the target blood vessel, and in a case where that the scene determined by the scene determination unit is an insertion scene where the insert punctures and is moving toward the target blood vessel, the region-of-interest detection unit may detect at least one of a distal end of the insert or a tissue positioned near the distal end of the insert inside the subject as the region of interest.

In this case, the insert may be a catheter with a puncture needle, and the scene determination unit may determine that the scene is the insertion scene in a case where the blood vessel of the subject and a distal end of the puncture needle are detected in the ultrasound image by analyzing the ultrasound image acquired by the image acquisition unit.

Alternatively, the image acquisition unit may continuously acquire the ultrasound images at a given frame rate, and the scene determination unit may analyze the ultrasound images of a plurality of frames continuously acquired by the image acquisition unit and may determine that the scene is the insertion scene in a case where a position of the insert is changed to approach the target blood vessel in the ultrasound images of the plurality of frames and in a case where an observation direction of the blood vessel and the insert is switched in the ultrasound images of the plurality of frames.

In the above-described configuration, a blood vessel into which an insert puncturing the subject is inserted, among blood vessels of the subject may correspond to the target blood vessel, and in a case where the scene determined by the scene determination unit is a placement scene where a distal end part of the insert is placed inside the target blood vessel, the region-of-interest detection unit may detect the distal end part of the insert or a lesion portion inside the subject as the region of interest.

In this case, the insert may be a catheter with a puncture needle, and the scene determination unit may determine that the scene is the placement scene in a case where a distal end part of the catheter present inside the blood vessel in a state in which the puncture needle is removed is detected in the ultrasound image by analyzing the ultrasound image acquired by the image acquisition unit.

Alternatively, the image acquisition unit may continuously acquire the ultrasound images at a given frame rate, and the scene determination unit may analyze the ultrasound images of a plurality of frames continuously acquired by the image acquisition unit and may determine that the scene is the placement scene in a case where appearance and disappearance of the distal end part of the insert are repeated in the ultrasound images of the plurality of frames and in a case where appearance and disappearance of the lesion portion inside the subject are repeated in the ultrasound images of the plurality of frames.

In the ultrasound diagnostic apparatus of the present invention described above, in a case where a plurality of the target blood vessels in the ultrasound image are detected, the blood vessel information acquisition unit may acquire the blood vessel information on each of the plurality of the detected target blood vessels, and the blood vessel information display unit may simultaneously display the blood vessel information of each of the plurality of the target blood vessels acquired by the blood vessel information acquisition unit within the display range. Then, it is preferable that, in a case where the region of interest is detected by the region-of-interest detection unit, the apparatus controller decides the display region for each target blood vessel based on the position of the region of interest such that the blood vessel information of each of the plurality of the target blood vessels is displayed separately.

The ultrasound diagnostic apparatus of the present invention described above may further comprise a highlighting unit that detects the target blood vessel in the ultrasound image by analyzing the ultrasound image acquired by the image acquisition unit and fills the detected target blood vessel in the ultrasound image with a highlight color to highlight the target blood vessel. In this case, it is more preferable that the apparatus controller performs control such that the highlighting unit and the blood vessel information display unit set a color of the display region of the blood vessel information and the highlight color in highlighting the target blood vessel to the same color.

The ultrasound diagnostic apparatus of the present invention may further comprise an ultrasound probe having the transducer array, and a processor to which the ultrasound probe is connected. In this case, the image acquisition unit may be configured with a transmission circuit that causes the transducer array to transmit the ultrasound beam toward the subject, a reception circuit that processes a signal output from the transducer array having received the ultrasound echo generated inside the subject to generate a sound ray signal, and an image generation unit that generates the ultrasound image based on the sound ray signal generated by the reception circuit, and each of the transmission circuit, the reception circuit, and the image generation unit may be provided in the ultrasound probe or the processor.

To achieve the above-described object, the present invention provides a method of controlling an ultrasound diagnostic apparatus that displays a blood vessel of a subject in an ultrasound image, the method comprising causing transmission of an ultrasound beam from a transducer array toward the subject and receiving an ultrasound echo by the subject to acquire the ultrasound image, displaying the acquired ultrasound image on a display device, detecting a target blood vessel in the ultrasound image by analyzing the acquired ultrasound image and acquiring blood vessel information including at least one of a diameter or a depth of the detected target blood vessel, displaying the acquired blood vessel information within a display range of the ultrasound image in the display device, detecting a region of interest in the ultrasound image to be noticed other than the target blood vessel by analyzing the acquired ultrasound image, and in a case where the region of interest is detected, deciding a display region of the blood vessel information in the display range based on a position of the region of interest and displaying the blood vessel information in the decided display region.

According to the present invention, it is possible to acquire the blood vessel information including at least one of the diameter or the depth of the target blood vessel by analyzing the ultrasound image including the target blood vessel. In displaying the blood vessel information within the display range of the ultrasound image, the blood vessel information is displayed in the display range decided based on the position of the region of interest in the ultrasound image. With this, it is possible to display the blood vessel information in an appropriate region while considering the presence of the region of interest in the display range of the ultrasound image.

BRIEF DESCRIPTION OF THE DRAWINGS

FIG. 7 is a diagram showing a flow of scene determination based on a video.

DESCRIPTION OF THE PREFERRED EMBODIMENTS

Hereinafter, a plurality of specific embodiments (first embodiment to third embodiment) of the present invention will be described referring to the accompanying drawings. Note that the embodiments described below are merely examples for ease of understanding of the present invention, and are not intended to limit the present invention. That is, the present invention can be modified or improved from the embodiments described below without departing from the scope and spirit of the present invention. Of course, the present invention includes equivalents thereof.

In the following description, it is assumed that the upper and lower sides and the right and left sides of an ultrasound image are upper and lower sides and right and left sides when an operator views the ultrasound image in front view.

Figure 4:
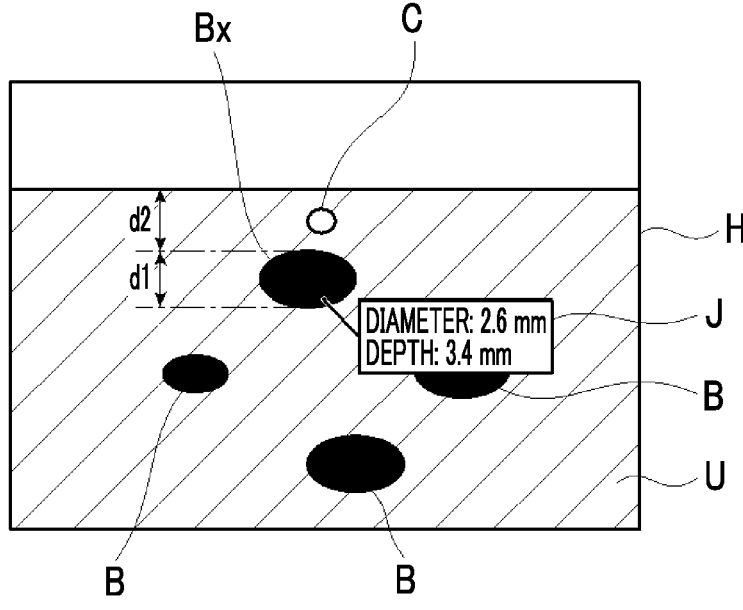
FIG. 4 is a schematic view of an ultrasound image that is displayed on a display device by the ultrasound diagnostic apparatus according to the first embodiment of the present invention.

For example, in an ultrasound image U shown in FIG. 4, an insert C is positioned upward of a blood vessel B.

Purpose of Ultrasound Diagnostic Apparatus of the Present Invention

In describing each embodiment of the present invention, the purpose of an ultrasound diagnostic apparatus of the present invention will be described.

The ultrasound diagnostic apparatus of the present invention is used in the procedure for inserting an insert, such as a puncture needle and a catheter, into a blood vessel of a subject while observing the inside of the subject, for example, an echo guided puncture method.

That is, the ultrasound diagnostic apparatus of the present invention is an apparatus that displays the blood vessel of the subject and the insert inserted into the blood vessel in an ultrasound image, and an operator of the insert appropriately observes the ultrasound image displayed by the ultrasound diagnostic apparatus during an insertion operation of the insert.

In the following description, unless otherwise specified, it is assumed that the ultrasound image is a B mode image (tomographic image) regarding a tissue inside the subject.

Hereinafter, although a case where the insert is a catheter with a puncture needle will be described as an example, the ultrasound diagnostic apparatus of the present invention can also be applied to a case where an insert other than the catheter with a puncture needle is inserted into the blood vessel. Here, the insert extends linearly, and can puncture a body surface and a vascular wall of the subject.

Hereinafter, a blood vessel satisfying a condition set in advance among blood vessels present inside the subject is referred to as a "target blood vessel", and the target blood vessel includes a blood vessel into which the insert puncturing the subject is inserted.

First Embodiment

Figure 1:
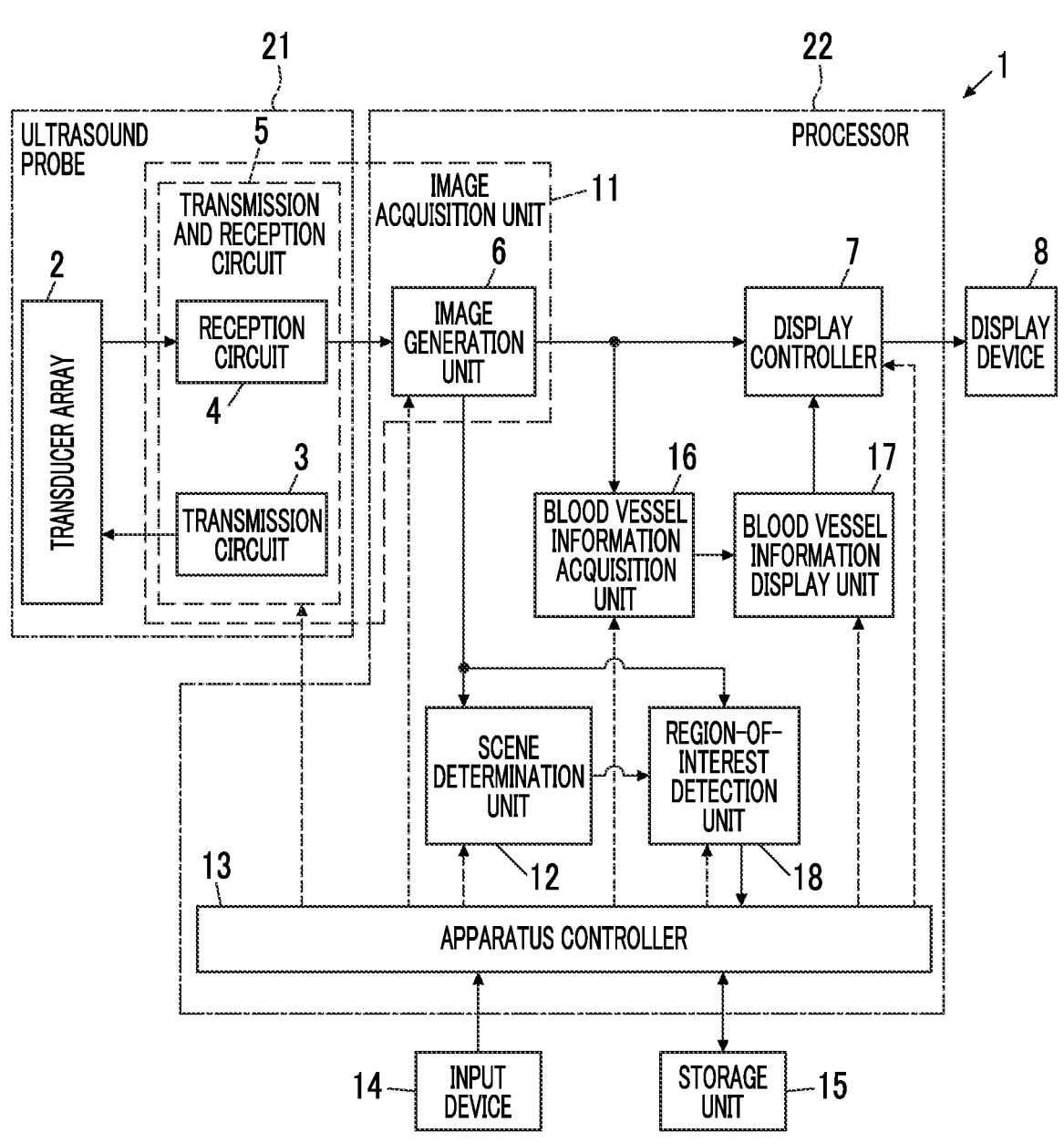
FIG. 1 is a block diagram showing the configuration of an ultrasound diagnostic apparatus according to a first embodiment of the present invention.

As shown in FIG. 1, an ultrasound diagnostic apparatus (hereinafter, referred to as an ultrasound diagnostic apparatus 1) according to the first embodiment of the present invention has an ultrasound probe 21 that comprises a transducer array 2, and a processor 22 that is connected to the ultrasound probe 21. Each of a transmission circuit 3 and a reception circuit 4 is connected to the transducer array 2. The transmission circuit 3 and the reception circuit 4 configure a transmission and reception circuit 5 and are included in the ultrasound probe 21 in the configuration shown in FIG. 1. An image generation unit 6 is connected to the reception circuit 4, a display controller 7 is connected to the image generation unit 6, and a display device 8 is connected to the display controller 7.

A scene determination unit 12, a blood vessel information acquisition unit 16, and a region-of-interest detection unit 18 are connected to the image generation unit 6, and a scene determination unit 12 is connected to the region-of-interest detection unit 18. A blood vessel information display unit 17 is connected to the blood vessel information acquisition unit 16, and the display controller 7 is connected to the blood vessel information display unit 17. An apparatus controller 13 is connected to each of the transmission and reception circuit 5, the image generation unit 6, the display controller 7, the scene determination unit 12, the blood vessel information acquisition unit 16, the blood vessel information display unit 17, and the region-of-interest detection unit 18, and the region-of-interest detection unit 18, an input device

14, and a storage unit 15 are connected to the apparatus controller 13. The apparatus controller 13 and the storage unit 15 are connected in a state in which information can be transferred therebetween.

In the configuration of FIG. 1, the image generation unit 6, the display controller 7, the scene determination unit 12, the apparatus controller 13, the blood vessel information acquisition unit 16, the blood vessel information display unit 17, and the region-of-interest detection unit 18 are provided in the processor 22. The transmission and reception circuit 5 (that is, the transmission circuit 3 and the reception circuit 4) of the ultrasound probe 21 and the image generation unit 6 of the processor 22 cooperate with each other to configure an image acquisition unit 11 that acquires an ultrasound image.

The transducer array 2 has a plurality of transducers arranged in a one-dimensional or two-dimensional manner. A plurality of transducers may be arranged linearly like a linear ultrasound probe or may be arranged in a curved manner like a convex or sector ultrasound probe. Each of a plurality of transducers transmits an ultrasonic wave in response to a drive signal supplied from the transmission circuit 3, receives an ultrasound echo generated inside the subject, and outputs an electric signal based on the ultrasound echo. Each transducer is configured by forming electrodes at both ends of a piezoelectric body consisting of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 causes the transducer array 2 to transmit an ultrasound beam toward the subject. Specifically, the transmission circuit 3 includes, for example, a plurality of pulse generators, and adjusts a delay amount of each drive signal to a plurality of transducers of the transducer array 2 based on a transmission delay pattern selected in response to a control signal from the apparatus controller 13 and supplies the drive signals to a plurality of transducers. Each drive signal is a pulsed or continuous-wave voltage signal, and in a case where the drive signal is applied to the electrodes of each transducer of the transducer array 2, the piezoelectric body expands and contracts. As a result, a pulsed or continuous-wave ultrasonic wave is generated from each transducer, and an ultrasound beam is formed from a combined wave of the ultrasonic waves.

The transmitted ultrasound beam is reflected by, for example, each part (for example, an organ and a blood vessel) inside the subject and appliance disposed inside the subject. With this, an ultrasound echo is generated and propagates inside the subject toward the transducer array 2, and is finally received by a plurality of transducers of the transducer array 2. In this case, each transducer expands and contracts with the reception of the ultrasound echo to generate an electric signal, and outputs the electric signal to the reception circuit 4.

Figure 2:
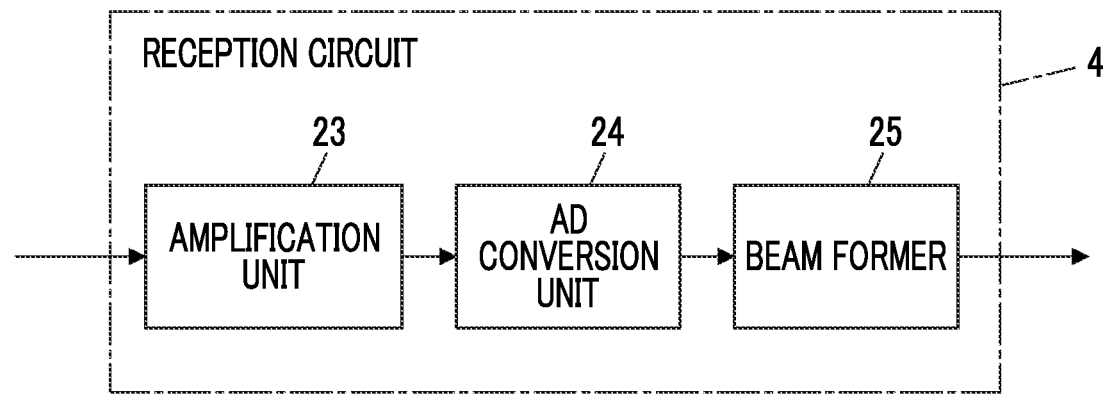
FIG. 2 is a block diagram showing the internal configuration of a reception circuit according to the first embodiment of the present invention.

The reception circuit 4 executes processing on a signal (strictly, an analog electric signal) output from the transducer array 2 in response to a control signal from the apparatus controller 13 to generate a sound ray signal. For example, as shown in FIG. 2, the reception circuit 4 has a configuration in which an amplification unit 23, an analog-digital (AD) conversion unit 24, and a beam former 25 are connected in series.

The amplification unit 23 amplifies a signal output from each of a plurality of transducers of the transducer array 2 and transmits the amplified signal to the AD conversion unit 24. The AD conversion unit 24 converts the amplified signal into digital reception data and transmits each piece of converted reception data to the beam former 25. The beam former 25 executes reception focus processing of giving a delay to each piece of reception data converted by the AD conversion unit 24 conforming to a sound speed or a distribution of a sound speed set based on a reception delay pattern selected in response to a control signal from the apparatus controller 13 and performing addition. With the reception focus processing, each piece of reception data converted by the AD conversion unit 24 is subjected to phasing addition, and a sound ray signal in which a focus of the ultrasound echo is narrowed is acquired.

Figure 3:
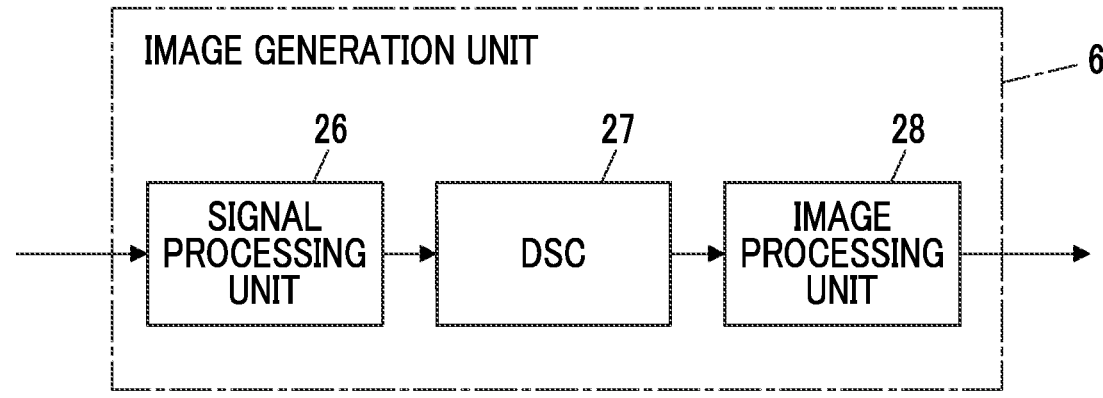
FIG. 3 is a block diagram showing the internal configuration of an image generation unit according to the first embodiment of the present invention.

The image generation unit 6 generates an ultrasound image based on the sound ray signal generated by the reception circuit 4, and as shown in FIG. 3, has a configuration in which a signal processing unit 26, a digital scan converter (DSC) 27, and an image processing unit 28 are sequentially connected in series.

The signal processing unit 26 performs correction of attenuation on the sound ray signal generated by the reception circuit 4 due to a distance depending on a depth of a reflection position of the ultrasonic wave, and then, executes envelope detection processing, thereby generating a B mode image signal indicating an ultrasound image.

The DSC 27 converts (raster-converts) the B mode image signal generated by the signal processing unit 26 into an image signal conforming to a normal television signal scanning system.

The image processing unit 28 executes various kinds of necessary image processing, such as gradation processing, on the B mode image signal input from the DSC 27, and then, outputs the B mode image signal to the display controller 7 and the image analysis unit 9. The B mode image signal subjected to the image processing by the image processing unit 28 corresponds to an ultrasound image.

The apparatus controller 13 performs control such that the transmission and reception circuit 5 and the image generation unit 6 (in other words, the image acquisition unit 11) continuously acquire ultrasound images at a given frame rate multiple times in an acquisition period of the ultrasound image.

The display controller 7 executes predetermined processing on the ultrasound image generated by the image generation unit 6 (in other words, the ultrasound image acquired by the image acquisition unit 11) and displays the ultrasound image on the display device 8 under the control of the apparatus controller 13. As shown in FIG. 4, the ultrasound image (hereinafter, referred to as an ultrasound image U) displayed on the display device 8 is developed in a depth direction and a width direction. Here, the width direction of the ultrasound image U is a direction in which a plurality of scanning lines configuring the ultrasound image U are arranged. The depth direction of the ultrasound image U is a direction in which the scanning lines extend. Each portion in the ultrasound image U is displayed at a position depending on a distance (depth) from a body surface of the subject with which the ultrasound probe 21 is brought into contact, in the depth direction.

As the ultrasound probe 21 is moved in a state of being brought into contact with the subject, a part of a tomographic plane of which is observed is changed depending on the ultrasound image U, and a direction in bringing the ultrasound probe 21 into contact with the subject is changed. Thereby, it is possible to switch an observation direction of the blood vessel inside the subject and the insert. For example, in a case where the ultrasound probe 21 is brought into contact with the subject in an orientation in which a direction (that is, a scanning direction) in which a plurality of transducers are arranged in the transducer array 2 follows an extension direction of the blood vessel and the insert, that is, in a case where a major axis method (paralleling method) is employed, the longitudinal sections of the blood vessel and the insert are observed in the ultrasound image U. Here, the longitudinal section of each of the blood vessel and the insert means a cut section along the extension direction of each of the blood vessel and the insert.

On the other hand, in a case where the ultrasound probe 21 is brought into contact with the subject in an orientation in which the arrangement direction (scanning direction) of the transducers in the transducer array 2 crosses the extension direction of the blood vessel and the insert, that is, in a case where a minor axis method (crossover method) is employed, as shown in FIG. 4, the transverse sections of the blood vessel B and the insert C are observed in the ultrasound image U. Here, the transverse section of each of the blood vessel and the insert means a cut section perpendicular to the extension direction of each of the blood vessel and the insert.

The display device 8 displays the ultrasound image U and the like under the control of the display controller 7, and includes, for example, a display, such as a liquid crystal display (LCD) or an organic electroluminescence display (organic EL display).

As shown in FIG. 4 and the like, blood vessel information J is displayed on the display device 8 along with the ultrasound image U. The blood vessel information J is described in, for example, a dialog box type display object as shown in FIG. 4, and may be displayed on the ultrasound image U in a superimposed manner or may be embedded and displayed as a part of the ultrasound image U.

The scene determination unit 12 determines a scene in a case where the ultrasound image U is acquired, by analyzing the ultrasound image U generated by the image generation unit 6 (in other words, the ultrasound image acquired by the image acquisition unit 11) with a known image processing technique. Examples of the scene that can be determined by the scene determination unit 12 include, for example, a search scene where a target blood vessel Bx is searched, an insertion scene where a catheter with a puncture needle as the insert C punctures and is inserted toward the target blood vessel Bx, and a placement scene where a distal end part of the insert C is placed inside the target blood vessel Bx.

The search scene is a scene at a stage before the insert C is inserted, and in this case, the operator is in a situation of moving the ultrasound probe 21 on the body surface of the subject to search for the target blood vessel Bx in the ultrasound image U.

The insertion scene is a scene until the distal end of the insert C reaches the target blood vessel Bx after puncturing the body surface of the subject, and in this case, the operator confirms the ultrasound image U while inserting the insert C and switches the orientation of the ultrasound probe 21 to change the observation direction of the blood vessel B and the insert C as needed. Along with this, the cross sections of the blood vessel B and the insert C rendered in the ultrasound image U are switched between the longitudinal sections (the cross sections in the major axis method) and the transverse sections (the cross sections in the minor axis method).

The placement scene is a scene at a stage where a distal end of the catheter with a puncture needle as the insert C, that is, a distal end of the puncture needle breaks through a vascular wall of the target blood vessel Bx to enter the target blood vessel Bx along with the distal end part of the catheter, then, the puncture needle is removed, and the distal end part of the catheter is placed inside the target blood vessel Bx. In this case, the distal end part of the insert C is only the distal end part of the catheter since the puncture needle is removed from the inside of the catheter. Thus, the transverse section (for example, see FIG. 4) of the distal end part of the insert C that previously appears as a circular shape with the presence of the puncture needle is separated in a lip shape and is configured with a pair of fragment images (for example, see FIG. 8).

In determining the scene, the scene determination unit 12 may analyze a video of ultrasound images U acquired by the image generation unit 6 at a given frame rate (in other words, ultrasound images U of a plurality of frames continuously acquired by the image acquisition unit 11) or may analyze a static image of an ultrasound image U (that is, an ultrasound image U of one frame). That is, in the first embodiment, the scene determination unit 12 can analyze the ultrasound images U as a video to determine the scene, and can also analyze the ultrasound image U as a static image to determine the scene.

The scene determination by the scene determination unit 12 will be described in detail in the following paragraph.

The blood vessel information acquisition unit 16 detects the target blood vessel Bx in the ultrasound image U through analysis and acquires blood vessel information including at least one of the diameter or the depth of the detected target blood vessel Bx.

The blood vessel information acquisition unit 16 analyzes the ultrasound image U generated by the image generation unit 6 (in other words, the ultrasound image U acquired by the image acquisition unit 11) conforming a known algorithm, thereby detecting the blood vessel B in the ultrasound image U. For example, the blood vessel information acquisition unit 16 can store typical pattern data of a blood vessel region as a template in advance, can calculate similarity to the pattern data while searching the ultrasound image U with the templates, and can regard that the blood vessel B is present at a location where the similarity is equal to or greater than a reference value and is the maximum.

In the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

The blood vessel information acquisition unit 16 measures the diameter and the depth of the blood vessel B by applying known image analysis processing to the detected blood vessel B in the ultrasound image U. Here, the diameter of the blood vessel B means the width (in FIG. 4, a length indicated by a symbol d1) of the blood vessel B in the depth direction of the ultrasound image U. The depth of the blood vessel B means the shortest distance (in FIG. 4, a distance indicated by a symbol d2) between a position in the ultrasound image U corresponding to the body surface of the subject and the blood vessel B in the depth direction.

In the first embodiment, although the blood vessel information acquisition unit 16 measures both of the diameter and the depth of the blood vessel B, the blood vessel information acquisition unit 16 may measure only one of the diameter and the depth. A feature quantity (for example, an area or the like) other than the diameter and the depth of the blood vessel B may be further measured.

The blood vessel information acquisition unit 16 specifies the blood vessel B having the measured values of the diameter and the depth within a predetermined range among the blood vessels B the diameter and the depth of which are measured, sets the specified blood vessel B as the target blood vessel Bx, and acquires the blood vessel information J indicating the measured values of the diameter and the depth of the target blood vessel Bx.

In the first embodiment, the blood vessel information acquisition unit 16 sets the blood vessel B the depth of which is comparatively small and the diameter of which is a size enough to insert the insert C, among the detected blood vessels B as the target blood vessel Bx and acquires the blood vessel information J of the target blood vessel Bx. Here, the target blood vessel Bx will be supplemented. The blood vessel B into which the insert C puncturing the subject is actually inserted, among the blood vessels B rendered in the ultrasound image U corresponds to the target blood vessel Bx. In this case, the size of the insert C may be decided in advance, and the blood vessel B having the diameter depending on the size may be selected. On the contrary, the intended blood vessel B may be decided, and the size of the insert C may be set depending on the diameter of the blood vessel B.

The blood vessel information J may indicate at least one of the diameter or the depth of the target blood vessel Bx or may indicate any one of the diameter or the depth.

The blood vessel information display unit 17 displays the blood vessel information J acquired by the blood vessel information acquisition unit 16 within a display range of the ultrasound image U in the display device 8 under the control of the display controller 7. The display range of the ultrasound image U is a range in which the ultrasound image U is actually displayed on an image display screen of the display device 8, and is, for example, a range inside a display frame of the ultrasound image U or a range in which a display window is rendered.

The region-of-interest detection unit 18 detects a region of interest in the ultrasound image U by analyzing the ultrasound image U generated by the image generation unit 6 (in other words, the ultrasound image U acquired by the image acquisition unit 11). The region of interest is a region to be noticed other than the target blood vessel Bx in the ultrasound image U and is different for each scene described above.

While a detection procedure of the region of interest by the region-of-interest detection unit 18 will be described below in detail, as an algorithm in detecting the region of interest, a known algorithm, such as template matching, a machine learning method, or a general image recognition method using deep learning, can be used.

The apparatus controller 13 performs control of each unit of the ultrasound diagnostic apparatus 1 based on a program stored in advance in the storage unit 15 or the like, information input from the operator through the input device 14, and the like.

In a case where the region of interest is detected in the ultrasound image U by the region-of-interest detection unit 18, the apparatus controller 13 decides a display region of the blood vessel information J within the display range of the ultrasound image U based on a position of the region of interest. Then, the apparatus controller 13 performs control such that the blood vessel information display unit 17 displays the blood vessel information J in the decided display region.

In detail, the apparatus controller 13 extracts a display candidate region avoiding the target blood vessel Bx and the region of interest within the display range of the ultrasound image U. Here, the display candidate region avoiding the target blood vessel Bx and the region of interest means a region where the blood vessel information J can be displayed not to overlap (not to cover) the target blood vessel Bx and the region of interest, and hereinafter, is simply referred to as a "display candidate region".

Then, the apparatus controller 13 decides the display region from the extracted display candidate region, in a case where only one display candidate region is extracted, decides the display candidate region as the display region, and in a case where a plurality of display candidate regions are extracted, decides a region closest to the target blood vessel Bx as the display region.

On the other hand, in a case where the display candidate region is not extracted within the display range of the ultrasound image U, the apparatus controller 13 decides the display region such that at least a part of the blood vessel information J overlaps the region of interest. More specifically, for example, in a case where the region-of-interest detection unit 18 detects a plurality of regions of interest in the ultrasound image U, the apparatus controller 13 sets priority to each of a plurality of regions of interest. In this case, the apparatus controller 13 sets the priority of each of a plurality of regions of interest in the display range of the ultrasound image U based on the position of each of a plurality of regions of interest. For example, the priority of each region of interest is set to increase in an order of lower, lower right, lower left, right, left, upper right, upper left, and upper.

A rule in setting the priority of each region of interest based on the position of each region of interest is stored in the storage unit 15, and the apparatus controller 13 reads out the above-described rule from the storage unit 15 in setting the priority of each region of interest.

Then, in a case where the display candidate region is not extracted within the display range of the ultrasound image U, the apparatus controller 13 decides the display region such that at least a part of the blood vessel information J overlaps a region of interest with lower priority (for example, a region of interest with the lowest priority).

The input device 14 is provided for the operator to perform an input operation, and can be configured with, for example, a keyboard, a mouse, a track ball, a touch pad, and a touch panel.

The priority set to each region of interest in a case where the region-of-interest detection unit 18 detects a plurality of regions of interest in the ultrasound image U may be input from the operator through the input device 14. In this case, since the apparatus controller 13 sets the priority of each region of interest based on input contents to the input device 14, it is possible to reflect user's intention or the like to freely set the priority of each region of interest.

The storage unit 15 stores a control program of the ultrasound diagnostic apparatus 1 and various kinds of information, and a recording medium, such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server computer, or the like can be used.

As described above, the storage unit 15 stores the rule in setting the priority to each region of interest in a case where the region-of-interest detection unit 18 detects a plurality of regions of interest in the ultrasound image U.

The storage unit 15 includes a cine memory (not shown), and the cine memory has a capacity for accumulating an ultrasound image (B mode image signal) for one frame or ultrasound images for several continuous frames. The apparatus controller 13 reads out the ultrasound image of one frame stored in the cine memory and transfers the ultrasound image to the display controller 7 in a freeze mode. With this, the ultrasound image U of one frame (that is, a static image) is displayed on the display device 8.

The processor 22 in which the image generation unit 6, the display controller 7, the scene determination unit 12, the blood vessel information acquisition unit 16, the apparatus controller 13, the blood vessel information display unit 17, and the region-of-interest detection unit 18 described above are provided is configured with, for example, a central processing unit (CPU) and a control program causing the CPU to execute various kinds of processing. The present invention is not limited thereto, and the processor 22 may be configured using a field programmable gate array (FPGA), a digital signal processor (DSP), an application specific integrated circuit (ASIC), a graphics processing unit (GPU), or other integrated circuits (ICs), or may be configured by combining such ICs.

The image generation unit 6, the display controller 7, the scene determination unit 12, the apparatus controller 13, the blood vessel information acquisition unit 16, the blood vessel information display unit 17, and the region-of-interest detection unit 18 provided in the processor 22 may be configured to be partially or wholly integrated into one CPU or the like.

The processor 22 may be mounted in, for example, a stationary type apparatus or may be mounted in a portable type apparatus, such as a notebook type personal computer (PC), a smartphone, or a tablet terminal.

Next, the operation of the ultrasound diagnostic apparatus 1 according to the first embodiment will be described in detail referring to a flowchart shown in FIG. 5.

In a display flow of an ultrasound image by the ultrasound diagnostic apparatus 1, Step S1 is executed, and in Step S1, the ultrasound image U is generated. Specifically, first, the ultrasound probe 21 is brought into contact with the body surface of the subject, an ultrasound beam is transmitted from each of a plurality of transducers of the transducer array 2 into the subject in response to the drive signals from the transmission circuit 3, and a reception signal is output from each transducer that receives the ultrasound echo, to the reception circuit 4 subject. Next, the reception signal received by the reception circuit 4 is amplified by the amplification unit 23, is AD-converted by the AD conversion unit 24, and then, is subjected to phasing addition by the beam former 25. As a result, a sound ray signal is generated. The sound ray signal is subjected to the envelope detection processing by the signal processing unit 26 in the image generation unit 6 to become a B mode image signal, and the B mode image signal is output to the display controller 7 through the DSC 27 and the image processing unit 28. With this, an ultrasound image U is generated (in other words, the ultrasound image U is acquired).

In next Step S2, the scene determination unit 12 determines the scene where the ultrasound image U is generated (acquired), by analyzing the generated (acquired) ultrasound image U. In the scene determination by the scene determination unit 12, there are a mode that is performed based on the ultrasound image U of one frame (that is, a static image) and a mode that is performed based on the continuously acquired ultrasound images U of a plurality of frames (that is, a video), and one of such modes is selected. The selection of the mode may be performed, for example, by the operator through the input device 14 or may be automatically performed based on an elapsed time from when the scene determination unit 12 starts the acquisition of the ultrasound image U.

Hereinafter, a flow of the scene determination in each mode will be described.

Scene Determination Based on Static Image

Figure 6:
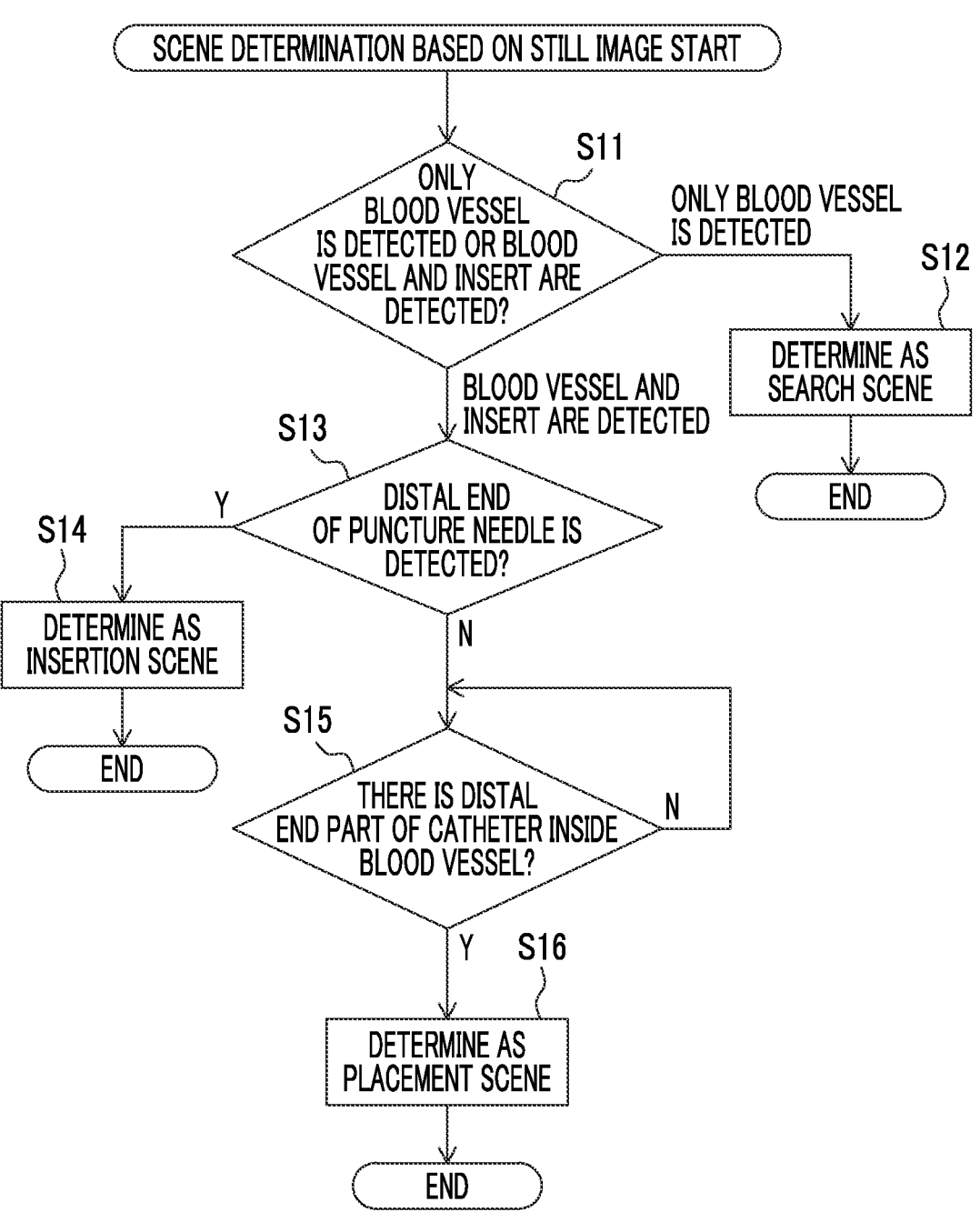
FIG. 6 is a diagram showing a flow of scene determination based on a static image.

In a case of determining the scene based on the static image, the scene determination unit 12 performs the determination along a flow shown in FIG. 6. First, the scene determination unit 12 executes Step S11, analyzes the ultrasound image U as the static image, and determines whether or not only the blood vessel B is detected in the ultrasound image U or whether or not the blood vessel B and the catheter with a puncture needle as the insert C are detected. In detecting the blood vessel B and the insert C in the ultrasound image U in Step S11, a known algorithm, such as template matching, a machine learning method, or a general image recognition method using deep learning, can be used.

In a case where only the blood vessel B is detected but the insert C is not detected in the ultrasound image U, Step S12, the scene determination unit 12 determines that the scene where the ultrasound image U as the static image is acquired is the search scene.

In a case where both of the blood vessel B and the insert C are detected in the ultrasound image U, the scene determination unit 12 executes Step S13 and determines whether or not the detected insert C is the distal end of the puncture needle. During the observation in the minor axis method (crossover method), the distal end of the puncture needle is rendered as a circular (in detail, a circular dot-shaped) image in the ultrasound image U. In light of this, the scene determination unit 12 determines whether or not the detected insert C is the distal end of the puncture needle, for example, using a method, such as image matching.

The determination about whether or not the detected insert C is the distal end of the puncture needle can also be performed using a method other than the above-described method. Specifically, there is a case where a part (non-distal end part) other than the distal end of the catheter with a puncture needle is rendered as an isolated dot-shaped image in the ultrasound image U. In this case, determination can be performed whether or not the image represents the distal end of the puncture needle based on whether or not acoustic shadow (shadow) appears behind the dot. That is, in a case where an image of a shaft part (non-distal end part) of the needle is rendered in the ultrasound image U, a sound wave is strongly reflected, and accordingly, acoustic shadow appears behind the image. In contrast, in a case where the image of the distal end of the needle is rendered in the ultrasound image U, the reflection of the sound wave is slightly weak, and acoustic shadow behind the image does not appear or is weakened. This is because a reflection area of the sound wave at the needle distal end is smaller than a reflection area in the shaft part for the reason that a needle tip is obliquely cut, the needle is thinned toward the distal end of the needle, or the like.

Incidentally, for the reason that the puncture needle with the needle distal end subjected to echogenic machining is deficient in practicability due to hardness of insertion or the like, in many cases, the shaft part slightly in front of the needle distal end is subjected to echogenic machining. Even in a case where such a puncture needle is used, with the determination based on acoustic shadow described above, the needle distal end and the non-distal end can be distinguished.

In a case where determination is made that the detected insert C is the distal end of the puncture needle, Step S14, the scene determination unit 12 determines that the scene where the ultrasound image U as the static image is acquired is the insertion scene.

Figure 8:
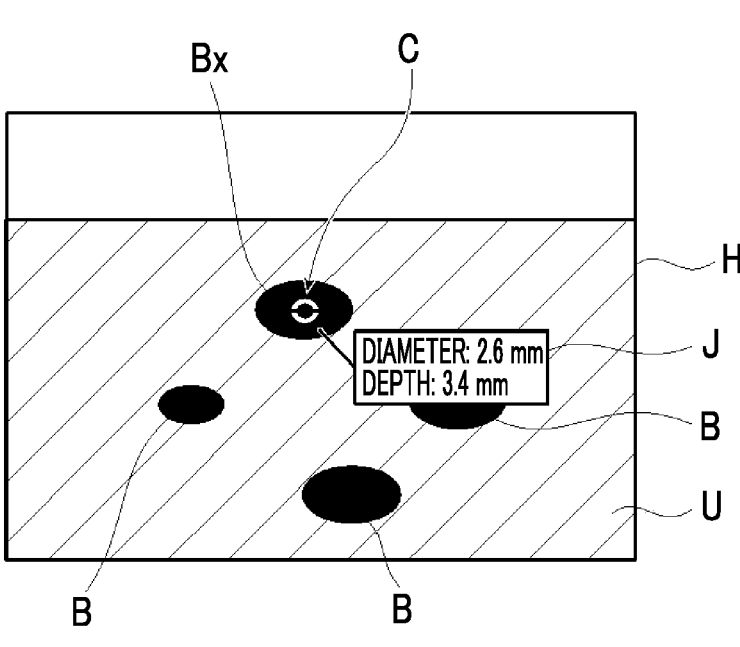
FIG. 8 is a diagram of an ultrasound image representing a situation in which a distal end part of a catheter is placed inside a blood vessel.

In a case where determination is made that the detected insert C is not the distal end of the puncture needle, the scene determination unit 12 executes Step S15 and determines whether or not the detected insert C is present inside the blood vessel B. In more detail, in Step S15, the scene determination unit 15 determines whether or not the distal end part of the catheter in a state in which the puncture needle is removed is present inside the blood vessel B. During the observation in the minor axis method (crossover method), as shown in FIG. 8, the distal end part of the catheter in a state in which the puncture needle is removed is separated in a lip shape and is rendered as a pair of fragment images in the ultrasound image U. In light of this, the scene determination unit 12 determines whether or not the detected insert C inside the blood vessel B is the distal end part of the catheter, for example, using a method, such as image matching.

In a case where determination is made that the detected insert C is the distal end part of the catheter that is present inside the blood vessel B in a state in which the puncture needle is removed, Step S16, the scene determination unit 12 determines that the scene where the ultrasound image U as the static image is acquired is the placement scene.

On the other hand, for example, in a case where the puncture needle is not yet removed from the catheter, or the like, the scene determination unit 12 determines that the distal end part of the catheter in a state in which the puncture needle is removed is not inside the blood vessel B. In this case, Step S15 is repeated.

With the procedure described above, based on the static image of the ultrasound image U of one frame, it is possible to appropriately determine the scene when the ultrasound image U is acquired.

Scene Determination Based on Video

Figure 9:
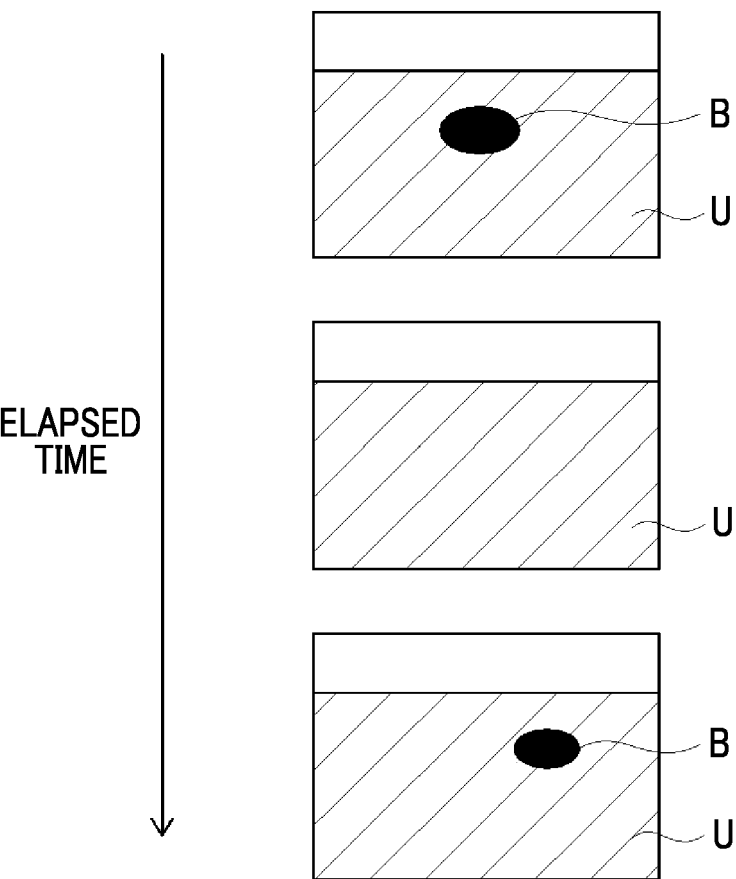
FIG. 9 is a diagram showing a state in which appearance and disappearance of a blood vessel are repeated in a video of ultrasound images.

In determining the scene based on a video, the scene determination unit 12 performs the determination along a flow shown in FIG. 7. First, the scene determination unit 12 executes Step S21, analyzes the continuously acquired ultrasound images U of a plurality of frames, and determines whether or not appearance and disappearance of the blood vessel B are repeated in the ultrasound images U of a plurality of frames. Specifically, in Step S21, as shown in FIG. 9, the scene determination unit 12 determines whether or not the ultrasound image U in which the blood vessel B is detected and the ultrasound image U in which the blood vessel B is not detected are alternately switched within a short time in the ultrasound images U of a plurality of frames. In detecting the blood vessel B, the insert C, a lesion portion E, and the like in the ultrasound image U, a known algorithm, such as template matching, a machine learning method, and a general image recognition method using deep learning, can be used.

The repetition of appearance and disappearance of the blood vessel B in the ultrasound images U of a plurality of frames means that the operator is in a situation of moving the ultrasound probe 21 to search for the blood vessel B (that is, the target blood vessel Bx) into which the insert C is to be inserted. Accordingly, in a case where determination is made that appearance and disappearance of the blood vessel B are repeated in the ultrasound images U of a plurality of frames, in Step S22, the scene determination unit 12 determines that the scene where the ultrasound images U of a plurality of frames are acquired is the search scene.

On the other hand, in a case where the blood vessel B is detected in all the ultrasound images U of a plurality of frames, the scene determination unit 12 executes Step S23, analyzes the continuously acquired ultrasound images U of a plurality of frames, and determines whether or not the position of the blood vessel B is changed in the ultrasound images U of a plurality of frames.

The change of the position of the blood vessel B in the ultrasound images U of a plurality of frames means that the positions of the blood vessel B and other tissues rendered in the ultrasound images U are unstable, and the operator is in a situation of moving the ultrasound probe 21 to search for the blood vessel B (target blood vessel Bx) into which the insert C is to be inserted. Accordingly, in a case where determination is made that the position of the blood vessel B is changed in the ultrasound images U of a plurality of frames, the scene determination unit 12 executes Step S22 and determines that the scene where the ultrasound images U of a plurality of frames are acquired is the search scene.

In a case where the position of the blood vessel B is stable (not changed) in the ultrasound images U of a plurality of frames, the scene determination unit 12 executes Step S24, analyzes the continuously acquired ultrasound images U of a plurality of frames, and determines whether or not a position of the distal end of the insert C is changed to approach the target blood vessel Bx in the ultrasound images U of a plurality of frames. Here, the target blood vessel Bx is the blood vessel B that is positioned on a path of the insert C and into which the insert C is to be inserted later, among the blood vessels B in the ultrasound image U. Upon specifying the target blood vessel Bx, the scene determination unit 12 analyzes the ultrasound images U of a plurality of frames to detect a trajectory of the distal end of the insert C and estimates the path of the insert C based on the detected trajectory.

Figure 10:
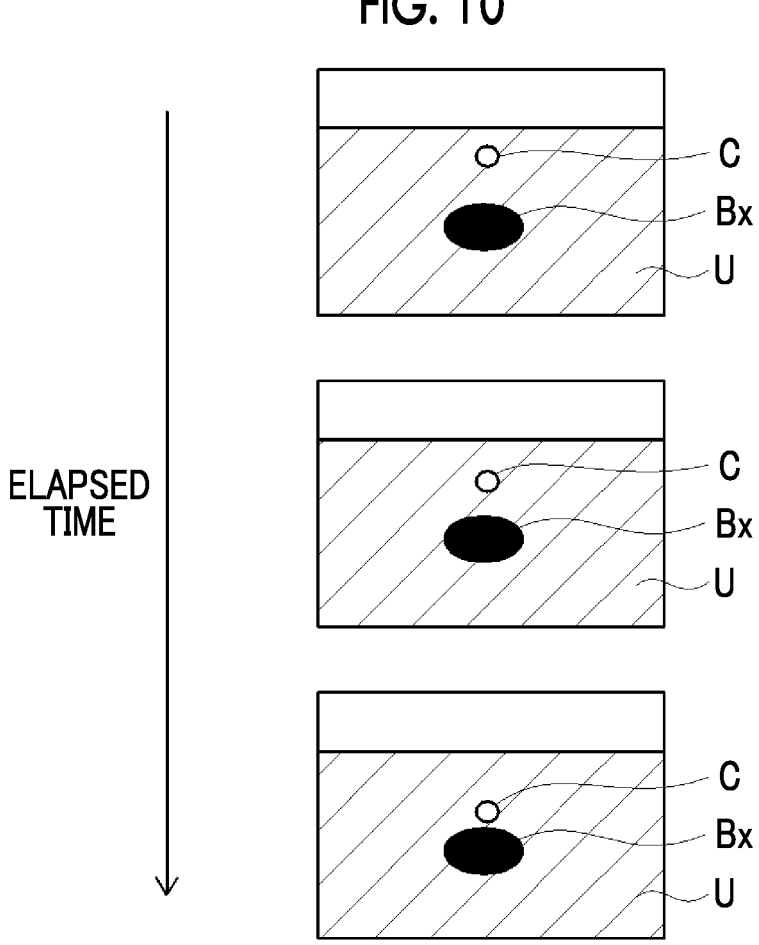
FIG. 10 is a diagram showing a state in which a distal end of an insert approaches a blood vessel in a video of ultrasound images.

In a case where determination is made that the position of the distal end of the insert C gradually approaches the target blood vessel Bx in the ultrasound images U of a plurality of frames as shown in FIG. 10, in Step S25, the scene determination unit 12 determines that the scene where the ultrasound images U of a plurality of frames are acquired is the insertion scene.

Figure 11:
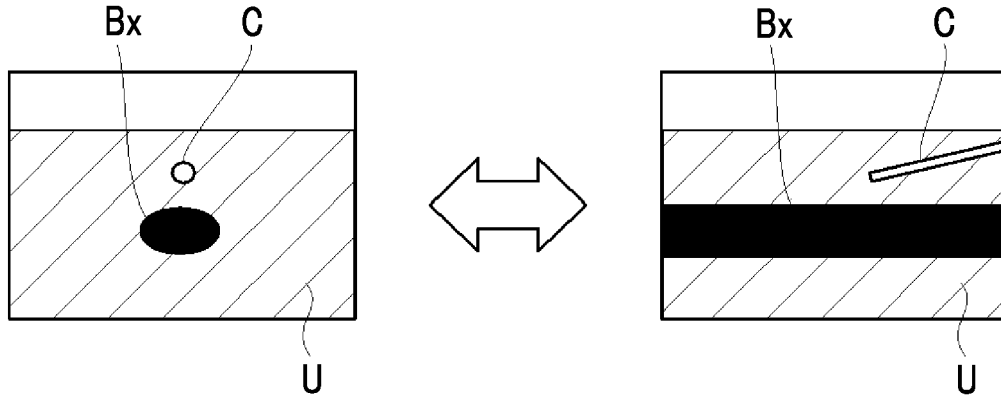
FIG. 11 is a diagram showing a state in which an observation direction of the blood vessel and the insert is switched in a video of ultrasound images.

On the other hand, there is a case where the operator changes the orientation of the ultrasound probe 21 to confirm that the insert C is appropriately inserted along an inner wall of the blood vessel B during an insertion operation of the insert C (that is, alternately employs the minor axis method and the major axis method) and switches the observation direction of the blood vessel B and the insert C as shown in FIG. 11. In this case, it may not be possible to clearly determine whether or not the distal end position of the insert C approaches the target blood vessel Bx in the ultrasound images U of a plurality of frames. In this case, the scene determination unit 12 executes Step S26, analyzes the continuously acquired ultrasound images U of a plurality of frames, and determines whether or not the observation direction of the blood vessel B and the insert C is switched a predetermined number of times or more in the ultrasound images U of a plurality of frames.

In a case where determination is made that the observation direction of the blood vessel B and the insert C is switched a predetermined number of times or more in the ultrasound images U of a plurality of frames, the scene determination unit 12 executes Step S25 and determines that the scene where the ultrasound images U of a plurality of frames are acquired is the insertion scene.

At a stage where the operation of the insert C is stable, and for example, the insert C is inserted into the target blood vessel Bx, the number of times the observation direction of the blood vessel B and the insert C is switched is less than the predetermined number of times. In this case, the scene determination unit 12 executes next Step S27, analyzes the continuously acquired ultrasound images U of a plurality of frames, and determines whether or not appearance and disappearance of the distal end part of the catheter as the insert C are repeated in the ultrasound images U of a plurality of frames.

Figure 12:
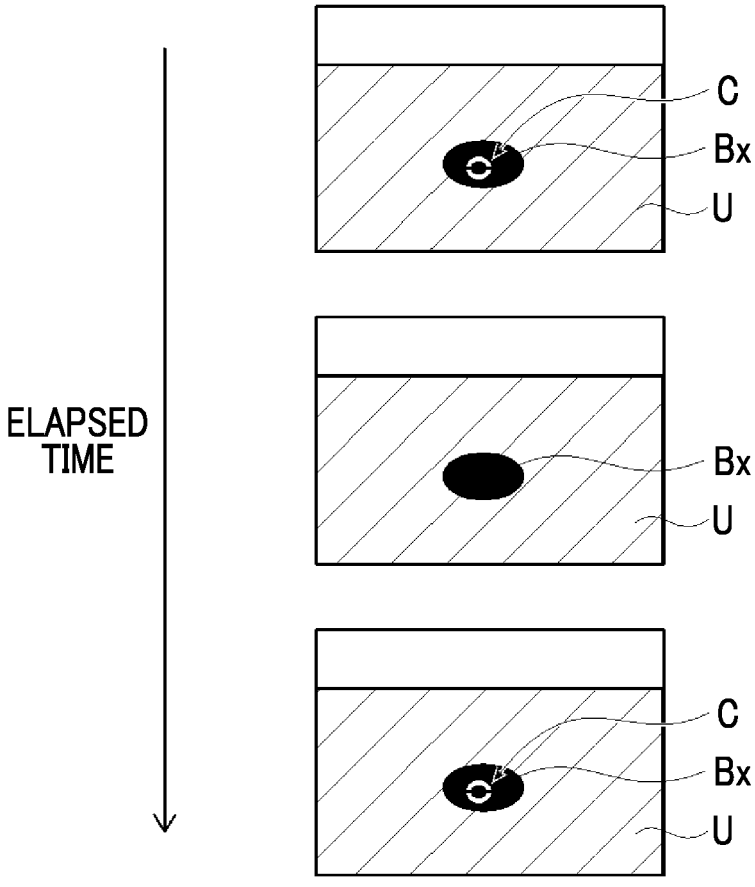
FIG. 12 is a diagram showing a state in which appearance and disappearance of the distal end part of the catheter are repeated in a video of ultrasound images.

The repetition of the appearance and disappearance of the distal end part of the catheter in the ultrasound images U of a plurality of frames means that the distal end part of the catheter is already placed inside the target blood vessel Bx as shown in FIG. 12 and the operator is in a situation of moving sweeping) the ultrasound probe 21 to confirm the distal end part of the catheter. Accordingly, in a case where determination is made that appearance and disappearance of the distal end part of the catheter are repeated in the ultrasound images U of a plurality of frames, in Step S28, the scene determination unit 12 determines that the scene where the ultrasound images U of a plurality of frames are acquired is the placement scene.

On the other hand, in a case where the distal end part of the catheter present inside the blood vessel B is detected in all the ultrasound images U of a plurality of frames, the scene determination unit 12 executes Step S29, analyzes the continuously acquired ultrasound images U of a plurality of frames, and determines whether or not appearance and disappearance of the lesion portion E (for example, phlebitis) inside the subject are repeated in the ultrasound images U of a plurality of frames.

Figure 13:
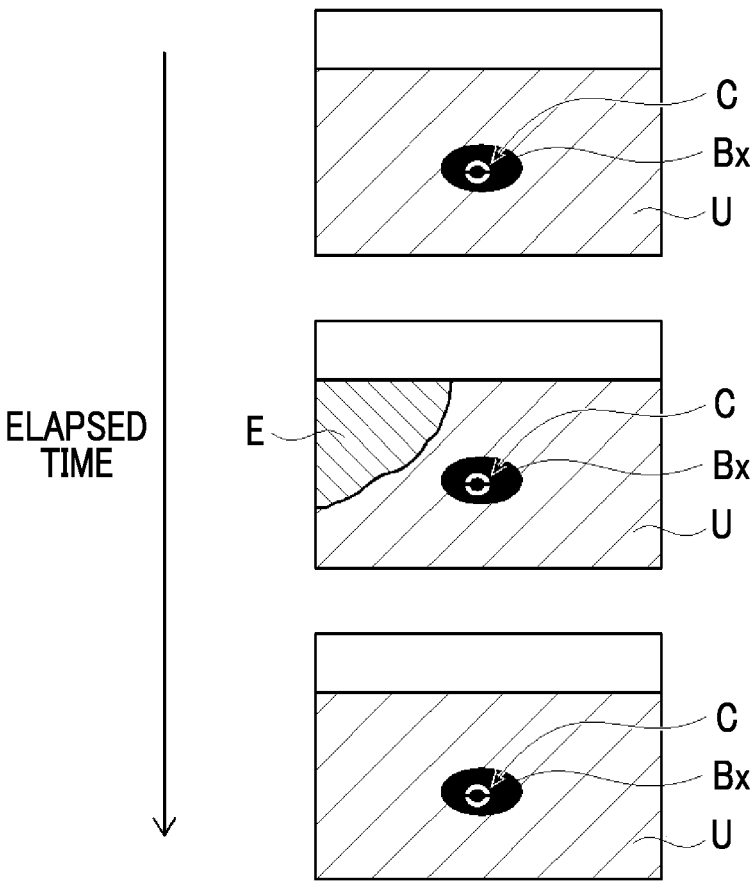
FIG. 13 is a diagram showing a state in which appearance and disappearance of a lesion portion inside a subject are repeated in a video of ultrasound images.

The repetition of appearance and disappearance of the lesion portion E in the ultrasound images U of a plurality of frames as shown in FIG. 13 means that the operator moves the ultrasound probe 21 to confirm the lesion portion E, such as phlebitis, caused by the placement of the distal end part of the catheter inside the blood vessel B. Accordingly, in a case where determination is made that appearance and disappearance of the lesion portion E are repeated in the ultrasound images U of a plurality of frames, the scene determination unit 12 executes Step S28 and determines that the scene where the ultrasound images U of a plurality of frames are acquired is the placement scene.

On the other hand, in a case where determination is made that appearance and disappearance of the lesion portion E are not repeated in the ultrasound images U of a plurality of frames, the process returns to Step S27, and the steps after S27 are repeated.

With the procedure described above, based on the continuously acquired ultrasound images U of a plurality of frames (that is, a video), it is possible to appropriately determine the scene where the ultrasound images U are acquired.

Figure 5:
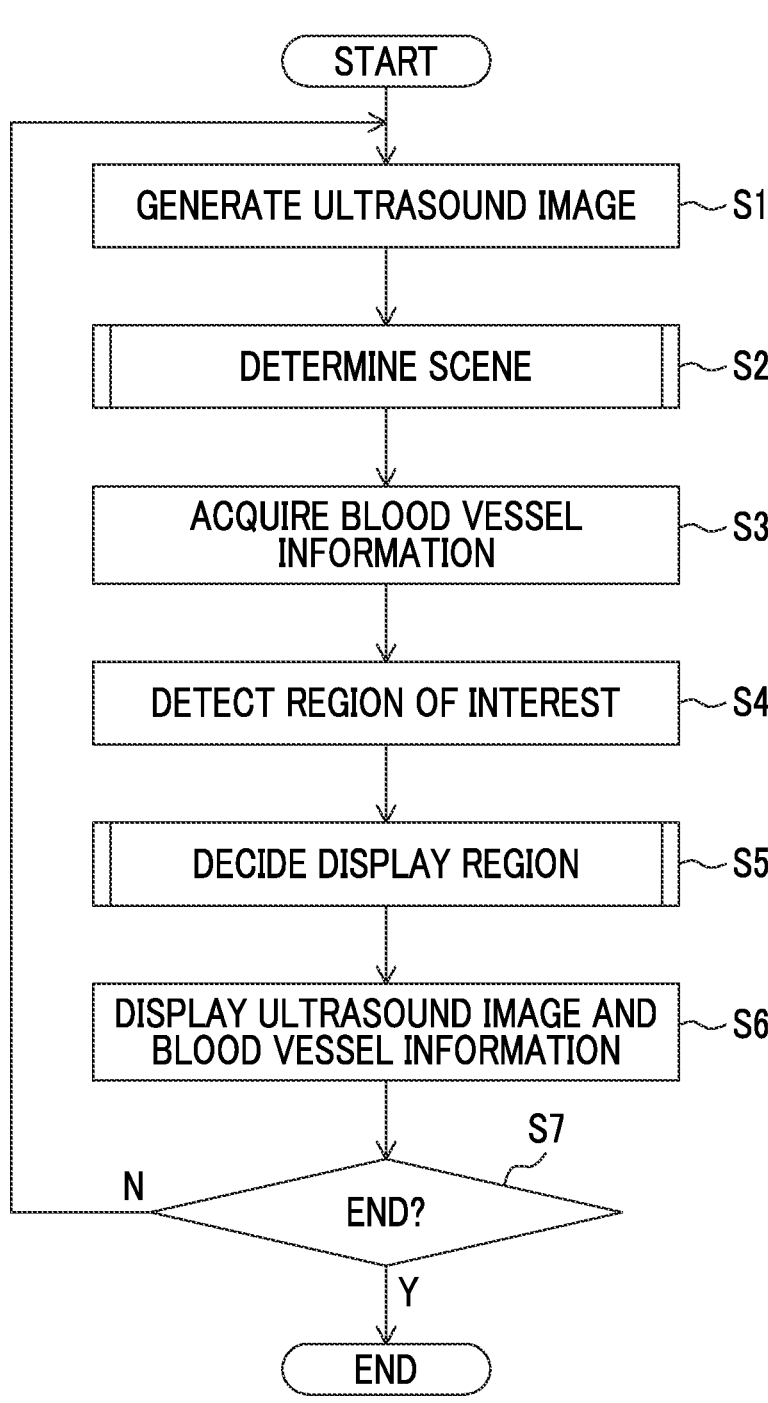
FIG. 5 is a flowchart illustrating the operation of the ultrasound diagnostic apparatus according to the first embodiment of the present invention.

Returning to the description on the flowchart of FIG. 5, Step S3 is executed after the execution of the scene determination. In Step S3, the blood vessel information acquisition unit 16 analyzes the ultrasound image U generated (acquired) in Step S1, detects the target blood vessel Bx in the ultrasound image U, and acquires the blood vessel information J of the detected target blood vessel Bx.

In subsequent Step S4, the region-of-interest detection unit 18 analyzes the ultrasound image U like the blood vessel information acquisition unit 16 and detects the region of interest in the ultrasound image U. In this case, the region-of-interest detection unit 18 detects the region of interest corresponding to the scene determined by the scene determination unit 12 in Step S2. Specifically, in a case where the scene determined by the scene determination unit 12 is the search scene, the region-of-interest detection unit 18 detects the lesion portion E inside the subject or the blood vessel B other than the target blood vessel Bx as the region of interest.

Figure 14:
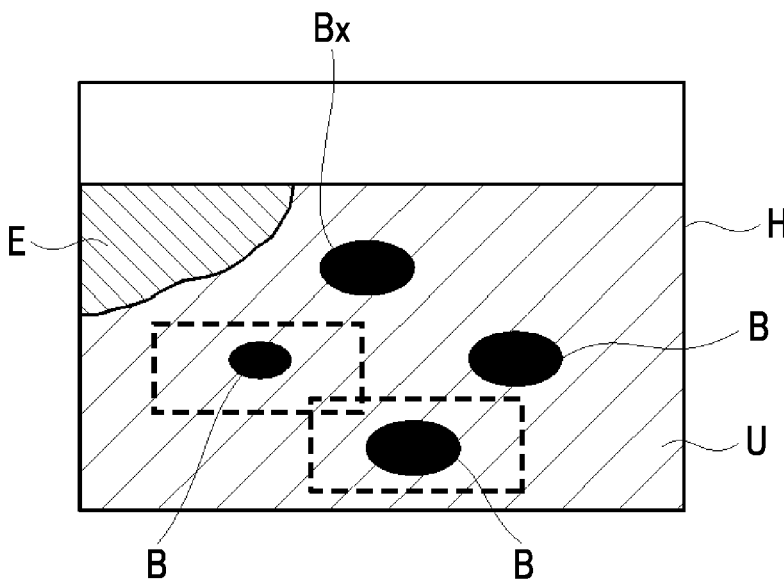
FIG. 14 is an explanatory view of a region of interest in an ultrasound image that is acquired on a search scene (first view).

In more detail, in a case where the scene is the search scene, and as shown in FIG. 14, the blood vessels B of various sizes are densely rendered in the ultrasound image U, the region-of-interest detection unit 18 detects the lesion portion E (for example, a blood clot or edema) in the ultrasound image U as the region of interest. In this case, the blood vessel B the depth of which is comparatively small and the diameter of which has a size enough to insert the insert C, among a plurality of blood vessels B in the ultrasound image U corresponds to the target blood vessel Bx.

Figure 15:
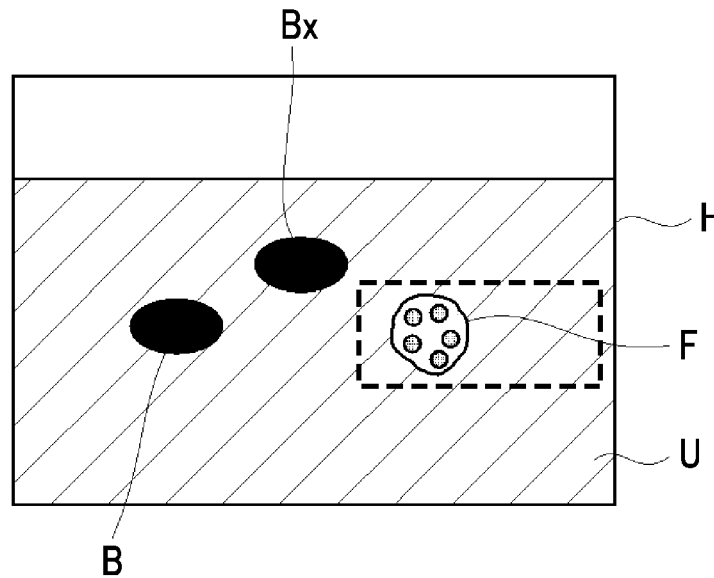
FIG. 15 is an explanatory view of the region of interest in the ultrasound image that is acquired on the search scene (second view).

In a case where the scene is the search scene, and as shown FIG. 15, the number of blood vessels B is small but various peripheral tissues F (for example, nerves, organs, and bones) are present around the blood vessel B in the ultrasound image U, the region-of-interest detection unit 18 detects the blood vessel B other than the target blood vessel Bx in the ultrasound image U as the region of interest. Even in this case, similarly to the ultrasound image U shown in FIG. 14, the blood vessel B the depth of which is comparatively small and the diameter of which has a size enough to insert the insert C corresponds to the target blood vessel Bx.

In a case where the scene determined by the scene determination unit 12 is the insertion scene, the region-of-interest detection unit 18 detects at least one of the distal end of the insert C or a tissue positioned near the distal end of the insert C inside the subject as the region of interest.

Figure 16:
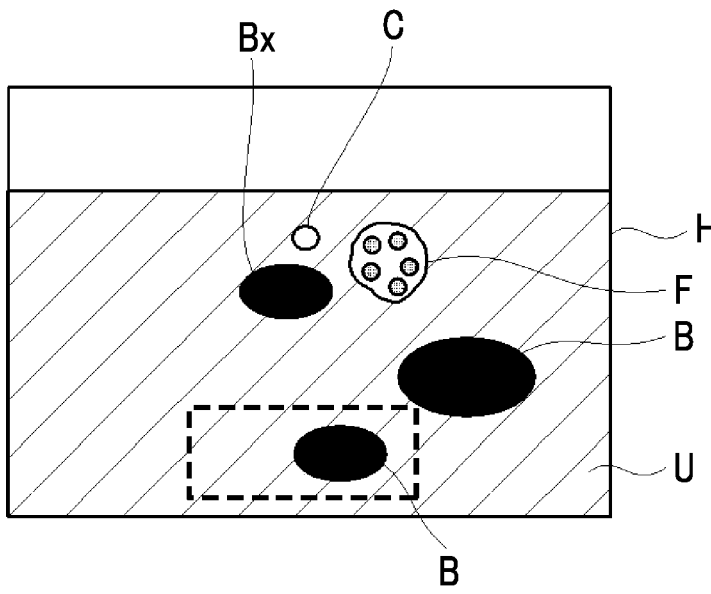
FIG. 16 is an explanatory view of a region of interest in an ultrasound image that is acquired on an insertion scene (first view).

In more detail, in a case where the scene is the insertion scene, and as shown in FIG. 16, the distal end (needle tip) of the catheter with a puncture needle as the insert C in the ultrasound image U is positioned near the target blood vessel Bx, the region-of-interest detection unit 18 detects the needle tip of the puncture needle in the ultrasound image U and the peripheral tissue F near the needle tip as the region of interest. The peripheral tissue F near the needle tip includes the blood vessel other than the target blood vessel Bx positioned near the needle tip.

Figure 17:
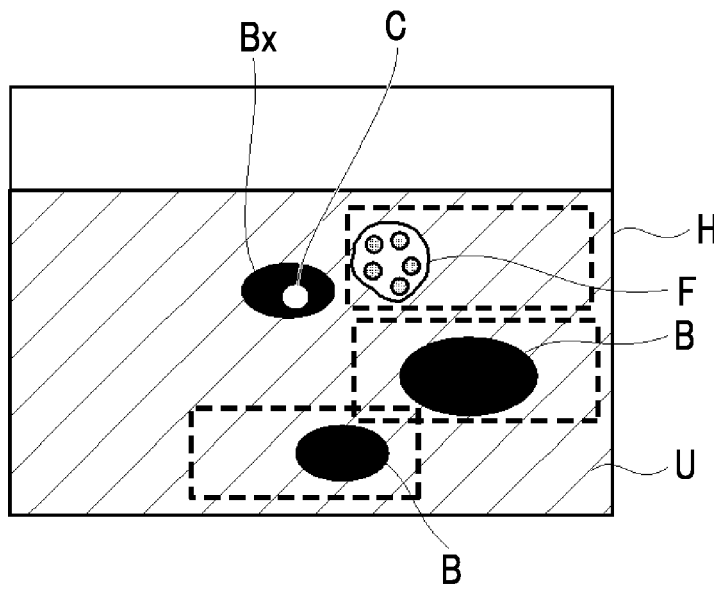
FIG. 17 is an explanatory view of the region of interest in the ultrasound image that is acquired on the insertion scene (second view).

In a case where the scene is the insertion scene, and as shown in FIG. 17, the distal end of the catheter with a puncture needle (that is, the distal end of the puncture needle) as the insert C in the ultrasound image U is inserted into the target blood vessel Bx, the region-of-interest detection unit 18 detects the needle tip of the puncture needle in the ultrasound image U as the region of interest.

In a case where the scene determined by the scene determination unit 12 is the placement scene, the region-of-interest detection unit 18 detects the distal end part of the insert C or the lesion portion E inside the subject as the region of interest.

Figure 18:
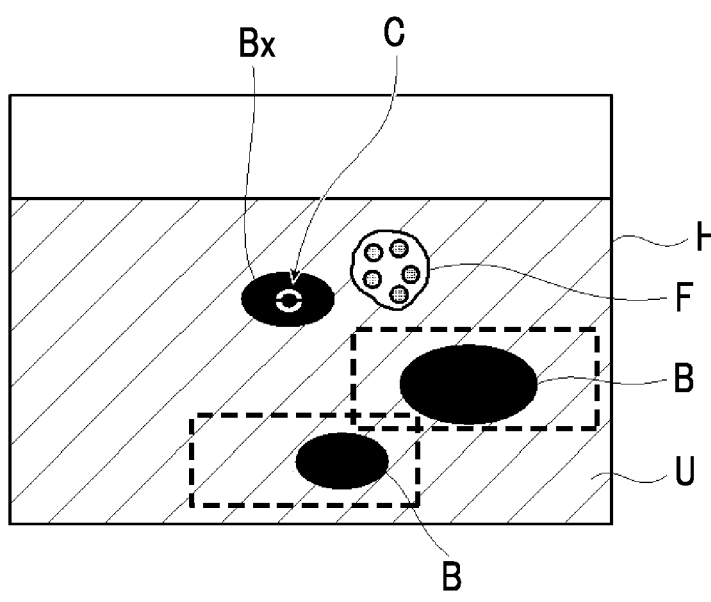
FIG. 18 is an explanatory view of a region of interest in an ultrasound image that is acquired on a placement scene (first view).

In more detail, in a case where the scene is the placement scene, and as shown in FIG. 18, the distal end part of the catheter in a state in which the puncture needle is removed, as the insert C in the ultrasound image U is present inside the target blood vessel Bx, the region-of-interest detection unit 18 detects the distal end part of the catheter in the ultrasound image U as the region of interest.

Figure 19:
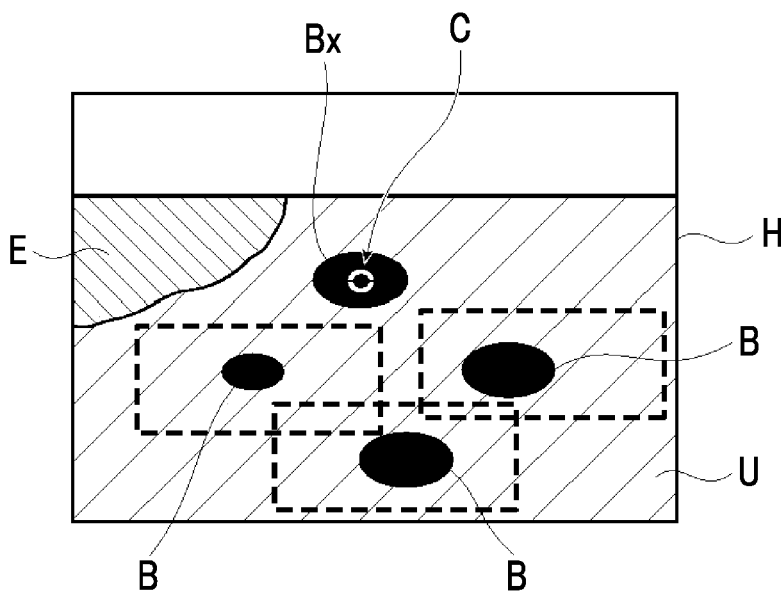
FIG. 19 is an explanatory view of the region of interest in the ultrasound image that is acquired on the placement scene (second view).

In a case where the scene is the placement scene, and as shown in FIG. 19, phlebitis as the lesion portion E is rendered near the target blood vessel Bx in which the distal end part of the catheter is placed, in the ultrasound image U, the region-of-interest detection unit 18 detects phlebitis in the ultrasound image U as the region of interest.

Figure 20:
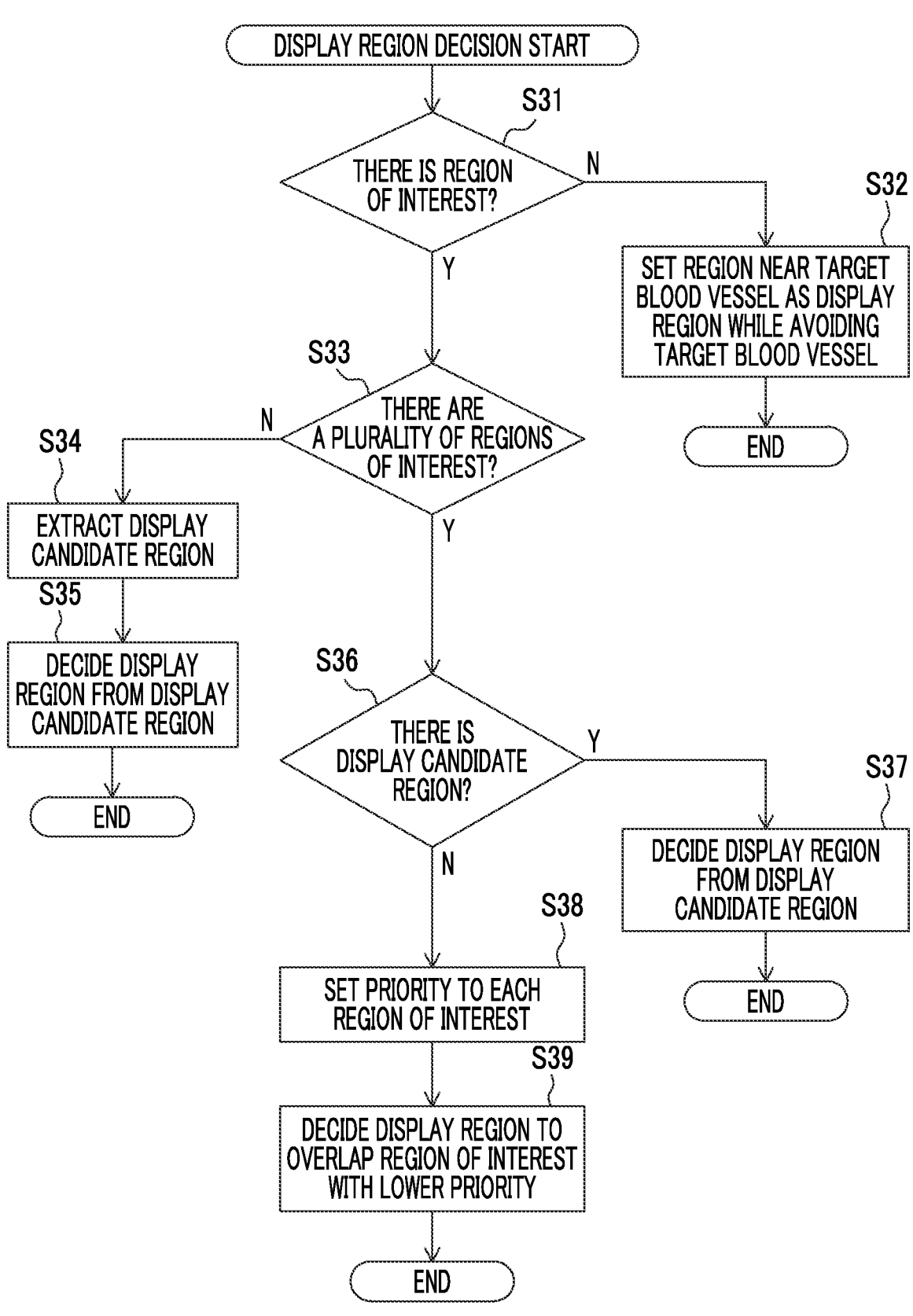
FIG. 20 is a diagram showing a flow of deciding a display region of blood vessel information.

After the detection of the region of interest is performed in the above-described manner, in Step S5, the apparatus controller 13 decides the display region of the blood vessel information J within a display range H of the ultrasound image U based on the position of the region of interest. Step S5 progresses following a flow shown in FIG. 20. Specifically, first, the apparatus controller 13 executes Step S31 and determines whether or not the region of interest in the ultrasound image U is detected by the region-of-interest detection unit 18 in previous Step S4.

In a case where determination is made that the region of interest is not detected, the apparatus controller 13 executes Step S32, and in Step S32, selects a region near the target blood vessel Bx while avoiding the target blood vessel Bx in the display range H of the ultrasound image U and decides the selected region as the display region.

On the other hand, in a case where determination is made that the region of interest is detected, in Step S33, the apparatus controller 13 determines whether or not there are a plurality of regions of interest detected by the region-of-interest detection unit 18. In a case where determination is made that only one region of interest is detected, the apparatus controller 13 executes Step S34 and extracts a display candidate region avoiding the target blood vessel Bx and the region of interest within the display range H of the ultrasound image U.

Here, a specific example of the display candidate region will be described. In the ultrasound image U that is acquired on the search scene and in which the blood vessels B of various sizes are densely rendered as shown in FIG. 14, a region where the blood vessel B the depth of which is comparatively great is rendered or a region where the blood vessel B the diameter of which is sufficiently smaller than the target blood vessel Bx is rendered is extracted as the display candidate region (in FIG. 14, a region indicated by a dotted line).

In the ultrasound image U that is acquired on the search scene and in which the number of blood vessels B is small but the peripheral tissues F is present around the blood vessels B as shown in FIG. 15, a region where the peripheral tissue F is rendered is extracted as the display candidate region (in FIG. 15, a region indicated by a dotted line).

In the ultrasound image U that is acquired on the insertion scene and in which the distal end of the catheter with a puncture needle as the insert C is positioned near the target blood vessel Bx as shown in FIG. 16, a region where the blood vessel B far from the distal end of the puncture needle is rendered is extracted as the display candidate region (in FIG. 16, a region indicated by a dotted line). In a case where the above-described ultrasound image U is an ultrasound image acquired in the major axis method, a region where the shaft part (not shown) of the puncture needle is rendered is extracted as the display candidate region.

In the ultrasound image U that is acquired on the insertion scene and in which the distal end of the catheter with a puncture needle as the insert C is inserted into the target blood vessel Bx as shown in FIG. 17, a region where the blood vessel B in which the puncture needle does not enter or the peripheral tissue F is rendered is extracted as the display candidate region (in FIG. 17, a region indicated by a dotted line). In a case where the above-described ultrasound image U is an ultrasound image acquired in the major axis method, a region where the shaft part (not shown) of the puncture needle is rendered is extracted as the display candidate region.

In the ultrasound image U that is acquired on the placement scene and in which the distal end part of the catheter in a state in which the puncture needle is removed is present inside the target blood vessel Bx as shown in FIGS. 18 and 19, a region where the blood vessel B in which the catheter does not enter is rendered is extracted as the display candidate region (in FIGS. 18 and 19, a region indicated by a dotted line). In a case where the above-described ultrasound image U is an ultrasound image acquired in the major axis method, a region where the shaft part of the catheter is rendered is extracted as the display candidate region.

Then, the apparatus controller 13 executes Step S35 after the execution of Step S34 and decides the display region of the blood vessel information J from the display candidate region extracted in Step S34. In this case, in a case where one display candidate region is extracted, the display candidate region may be decided as the display region of the blood vessel information J, and in a case where a plurality of display candidate regions are extracted, the display candidate region closest to the target blood vessel Bx among the display candidate regions may be decided as the display region of the blood vessel information J. Note that a method of deciding the display region from the display candidate region is not particularly limited, and for example, the display region may be decided from the display candidate region by any method.

On the other hand, in a case where determination is made in Step S33 that there are a plurality of regions of interest, the apparatus controller 13 executes Step S36 and determines whether or not the display candidate region is (can be extracted) within the display range H of the ultrasound image U. In a case where determination is made that there is the display candidate region, the apparatus controller 13 executes Step S37 and decides the display region of the blood vessel information J from the display candidate region.

In contrast, in a case where determination is made that the display candidate region is not (cannot be extracted) within the display range H of the ultrasound image U, the apparatus controller 13 executes Step S38. In Step S38, the apparatus controller 13 refers to the rule for setting the priority stored in the storage unit 15 and sets the priority to each of a plurality of detected regions of interest in compliance with the rule. In this case, the apparatus controller 13 sets the priority to each region of interest based on the position of each of a plurality of regions of interest in the display range H of the ultrasound image U.

After the setting of the priority, the apparatus controller 13 executes Step S39, and in Step S39, decides the display region such that at least a part of the blood vessel information J overlaps the region of interest with lower priority (for example, the region of interest with the lowest priority). With this, even though the display candidate region cannot be extracted within the display range of the ultrasound image U since a plurality of regions of interest are detected, it is possible to appropriately decide the display region of the blood vessel information J while considering the priority of each region of interest.

Returning to the description on the flowchart of FIG. 5, Step S6 is executed after the display region of the blood vessel information J is decided, and in Step S6, the ultrasound image U generated (acquired) in Step S1 is displayed on the display device 8 under the control of the display controller 7. In Step S6, the apparatus controller 13 performs control such that the blood vessel information display unit 17 displays the blood vessel information J in the display region decided in Step S5. With this, the blood vessel information J is displayed in the display region decided based on the position of the region of interest within the display range H of the ultrasound image U.

The process progresses to Step S7 after the execution of Step S6, and in Step S7, determination is made whether or not to end the operation of the ultrasound diagnostic apparatus 1. For example, in a case where the operator inputs an instruction for the guidance on ending the operation of the ultrasound diagnostic apparatus 1 through the input device 14 or the like, determination is made to end the operation of the ultrasound diagnostic apparatus 1, and in a case where the instruction to end the operation of the ultrasound diagnostic apparatus 1 is not input, determination is made not to end the operation of the ultrasound diagnostic apparatus 1. In a case where determination is made not to end the operation of the ultrasound diagnostic apparatus 1, the process returns to Step S1, the ultrasound image U is newly generated, and then, the steps after Step S2 are repeated.

On the other hand, in a case where determination is made to end the operation of the ultrasound diagnostic apparatus 1, the operation of the ultrasound diagnostic apparatus 1 ends.

As described above, with the ultrasound diagnostic apparatus 1 according to the first embodiment, the target blood vessel Bx (for example, the blood vessel B into which the insert C is to be inserted) in the ultrasound image U is detected, and the blood vessel information J indicating the diameter and the depth of the detected target blood vessel Bx is displayed in the display region decided based on the position of the region of interest within the display range H of the ultrasound image U.

In more detail, the blood vessel information J is displayed to overlap the target blood vessel Bx and the region of interest. With this, it is possible to confirm the target blood vessel Bx in the ultrasound image U and the blood vessel information J in real time, and simultaneously, it is possible to confirm the region of interest (for example, another blood vessel B present near the target blood vessel Bx) together.

That is, with the use of the ultrasound diagnostic apparatus 1 according to the first embodiment, it is possible to display the blood vessel information J at an appropriate position within the display range H of the ultrasound image U. In this case, for example, usability (convenience) for the operator is improved compared to a case where the blood vessel information J is constantly displayed in the same region within the display range H.

The region of interest can be changed depending on the scene in a case where the ultrasound image U is acquired. Thus, in the first embodiment, in light of this, the display region of the blood vessel information J is decided for each scene. With this, the display region of the blood vessel information J is appropriately decided corresponding to the scene at this point of time.

In the first embodiment, in a case where a plurality of regions of interest are detected in the ultrasound image U, and the blood vessel information J cannot be displayed while avoiding all of a plurality of regions of interest, the priority is set to each region of interest, and the display region is decided such that at least a part of the blood vessel information J overlaps the region of interest with lower priority.

With this, it is possible to display the blood vessel information J in the most appropriate display region.

In the above-described case, the transmission circuit 3 and the reception circuit 4 are provided in the ultrasound probe 21, and the image generation unit 6 is provided in the processor 22. The present invention is not limited thereto, and the transmission circuit 3, the reception circuit 4, and the image generation unit 6 may be provided in the ultrasound probe 21. In this case, the ultrasound image (B mode image signal) is generated by the ultrasound probe 21, and the processor 22 receives the ultrasound image sent from the ultrasound probe 21.

The transmission circuit 3 may be provided in the ultrasound probe 21, and the reception circuit 4 and the image generation unit 6 may be provided in the processor 22. Alternatively, the transmission circuit 3, the reception circuit 4, and the transmission and reception circuit 5 may be provided on the processor 22 side. In this case, the electric signal (analog signal) output from each of a plurality of transducers of the transducer array 2 that receives the ultrasound echo is transmitted from the ultrasound probe 21 to the processor 22, and the AD conversion of the electric signal, the generation of the sound ray signal, and the generation of the ultrasound image (B mode image signal) are performed on the processor 22 side.

Figure 21A:
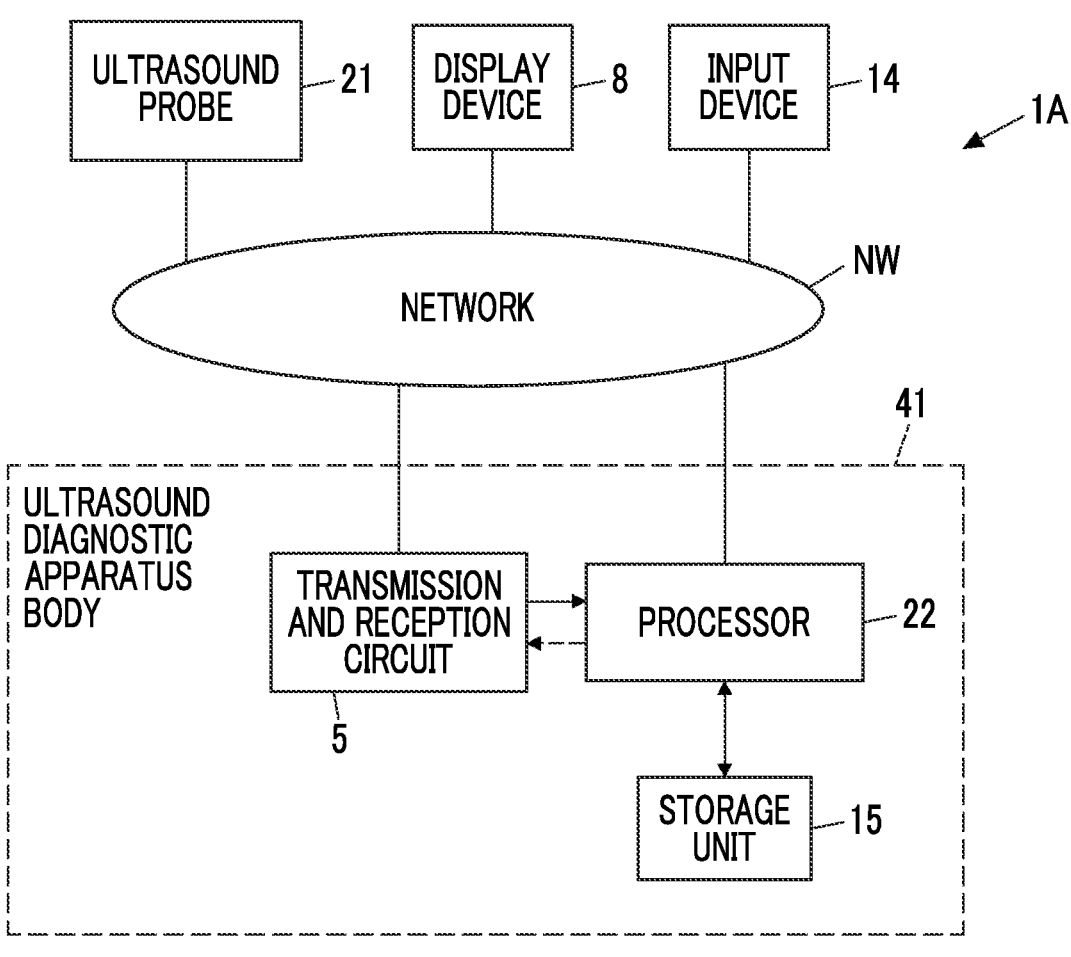
FIG. 21A is a diagram showing the configuration of an ultrasound diagnostic apparatus in which an ultrasound probe, a processor, a display device, and an input device are connected through a network.
Figure 21B:
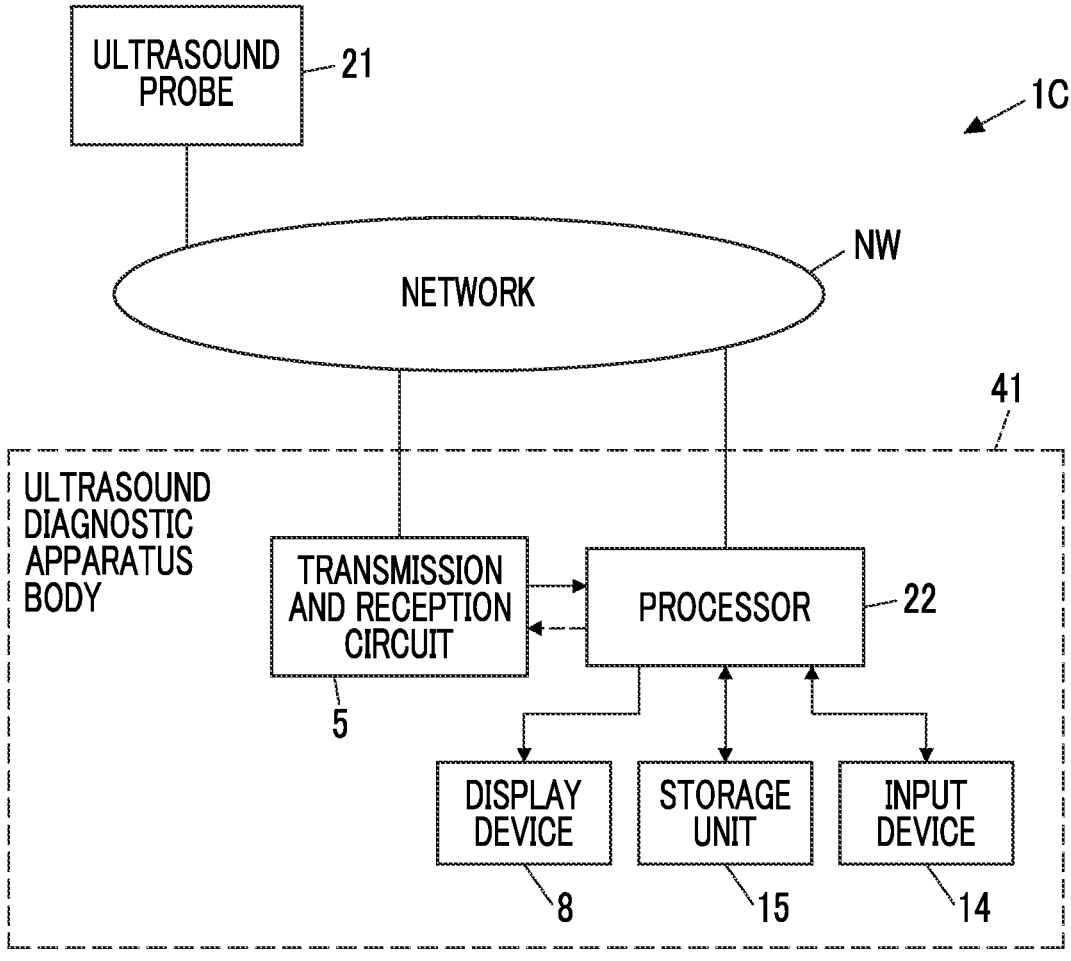
FIG. 21B is a diagram showing a configuration in which the ultrasound probe is connected to an ultrasound diagnostic apparatus body through the network.

In the above-described case, although a configuration in which the display device 8, the input device 14, and the ultrasound probe 21 are connected directly to the processor 22 has been described, for example, as shown in FIGS. 21A and 21B, a configuration may be made in which the display device 8, the input device 14, the ultrasound probe 21, and the processor 22 are connected indirectly through a network NW. In this case, the connection of each piece of equipment described above and the network NW may be wired connection or may be wireless connection.

In an ultrasound diagnostic apparatus 1A of the configuration shown in FIG. 21A, the display device 8, the input device 14, and the ultrasound probe 21 are connected to an ultrasound diagnostic apparatus body 41 through the network NW. The ultrasound diagnostic apparatus body 41 is not provided with the display device 8, the input device 14, and the ultrasound probe 21, and is configured with the transmission and reception circuit 5, the storage unit 15, and the processor 22, compared to the ultrasound diagnostic apparatus 1 of the configuration shown in FIG. 1.

In the ultrasound diagnostic apparatus 1A of the configuration shown in FIG. 21A, the above-described ultrasound diagnostic apparatus body 41 may be used as a remote server. In this case, for example, since the operator can diagnose the subject by preparing only the display device 8, the input device 14, and the ultrasound probe 21 at the hand of the operator, it is possible to improve convenience in ultrasound diagnosis.

In the ultrasound diagnostic apparatus 1A of the configuration shown in FIG. 21A, a smartphone or a tablet terminal may be used as the display device 8 and the input device 14. In this case, since the operator can more easily perform ultrasound diagnosis on the subject, it is possible to further improve convenience of ultrasound diagnosis.

In an ultrasound diagnostic apparatus 1C of the configuration shown in FIG. 21B, the display device 8 and the input device 14 are mounted in the ultrasound diagnostic apparatus body 41, and the ultrasound probe 21 is connected to the ultrasound diagnostic apparatus body 41 through the network NW. In this case, the ultrasound diagnostic apparatus body 41 may be configured with a remote server or can be configured with a smartphone or a tablet terminal.

Second Embodiment

Figure 22:
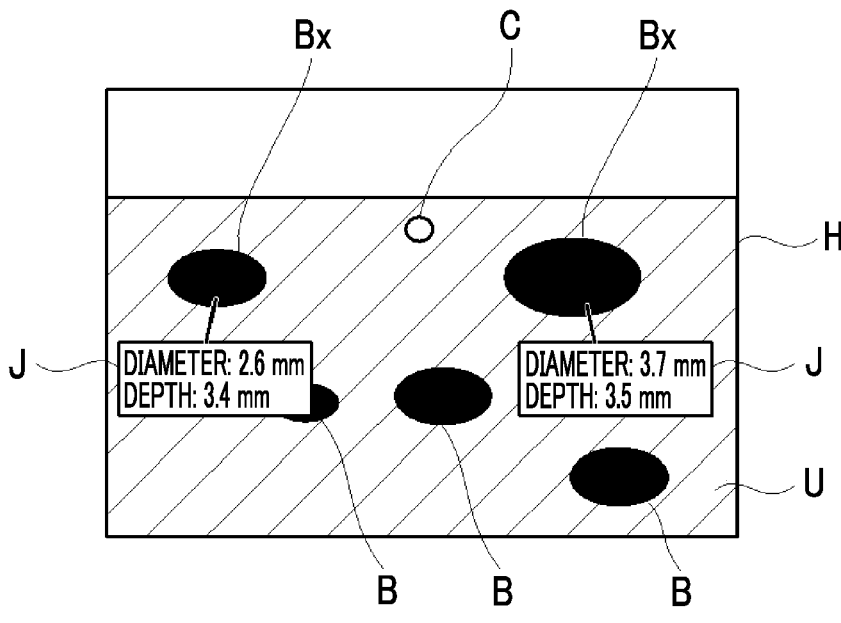
FIG. 22 is a diagram showing an ultrasound image that is displayed by an ultrasound diagnostic apparatus according to a second embodiment.

The number of target blood vessels Bx that are detected in the ultrasound image U is not limited to one, and it is also considered a case where a plurality of target blood vessels Bx are detected. In this case, at least one of the diameter or the depth can be measured on each of a plurality of target blood vessels Bx, and blood vessel information J regarding a measurement result can be acquired. Then, as shown in FIG. 22, the blood vessel information J of a plurality of target blood vessels Bx can be displayed simultaneously within the display range H of the ultrasound image U. Such an embodiment is referred to as a second embodiment, and the second embodiment will be described in detail.

The configuration of an ultrasound diagnostic apparatus according to the second embodiment is substantially the same as the configuration of the ultrasound diagnostic apparatus according to the above-described first embodiment. Hereinafter, the second embodiment will be described focusing on differences from the first embodiment.

In the second embodiment, in a case where a plurality of target blood vessels Bx in the ultrasound image U are detected, the blood vessel information acquisition unit 16 acquires the blood vessel information J on each of a plurality of detected target blood vessels Bx. Here, as in the first embodiment, each of a plurality of target blood vessels Bx is the blood vessel B the depth of which is comparatively small and the diameter of which has a size enough to insert the insert C.

In the second embodiment, the blood vessel information display unit 17 displays the blood vessel information J of a plurality of target blood vessels Bx acquired by the blood vessel information acquisition unit 16 within the display range H of the ultrasound image U simultaneously.

In the second embodiment, in a case where the region of interest in the ultrasound image U is detected by the region-of-interest detection unit 18, as in the first embodiment, the apparatus controller 13 decides the display region of the blood vessel information J based on the position of the region of interest. Although a procedure for deciding the display region of the blood vessel information J based on the position of the region of interest is generally common to the first embodiment, in deciding the display regions of a plurality of kinds of blood vessel information J, as shown in FIG. 22, the apparatus controller 13 decides the display region for each target blood vessel Bx such that the blood vessel information J of a plurality of target blood vessels Bx are displayed as far from one another as possible. In this case, a solution of a facility disposition problem may be applied, and the display region of each piece of blood vessel information J may be decided such that the blood vessel information J of a plurality of target blood vessels Bx are displayed in good balance within the display range H of the ultrasound image U.

Third Embodiment

In displaying the blood vessel information J of the target blood vessel Bx within the display range H of the ultrasound image U, the target blood vessel Bx can be highlighted such that the target blood vessel Bx is easily visible. Such an embodiment is referred to as a third embodiment, and the third embodiment will be described in detail referring to FIGS. 23 and 24.

Figure 23:
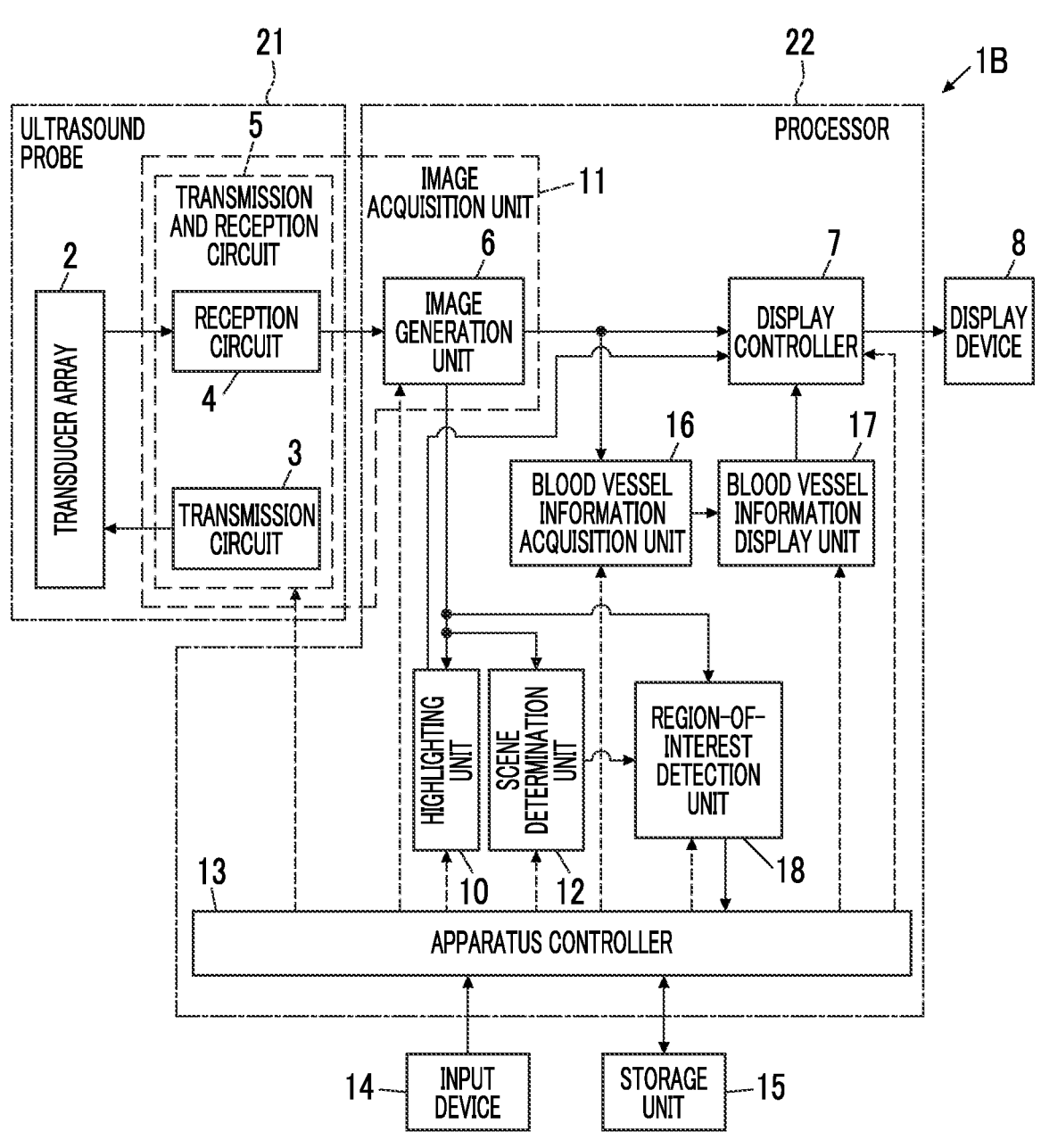
FIG. 23 is a block diagram showing the configuration of an ultrasound diagnostic apparatus according to a third embodiment.

In an ultrasound diagnostic apparatus 1B according to the third embodiment, as shown in FIG. 23, a highlighting unit 10 is added to the processor 22. The highlighting unit 10 is connected to the image generation unit 6, and the display controller 7 and the apparatus controller 13 are connected to the highlighting unit 10.

Figure 24:
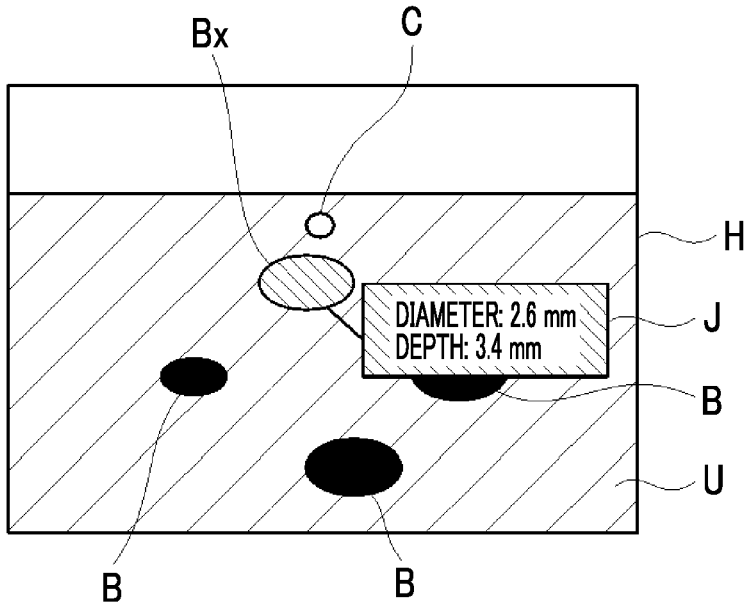
FIG. 24 is a diagram showing an ultrasound image that is displayed by the ultrasound diagnostic apparatus according to the third embodiment.

The highlighting unit 10 detects the target blood vessel Bx in the ultrasound image U by analyzing the ultrasound image U generated by the image generation unit 6 (in other words, the ultrasound image U acquired by the image acquisition unit 11) and fills the detected target blood vessel Bx with a highlight color to highlight the target blood vessel Bx as shown in FIG. 24. The highlight color is a color different from a color other than the target blood vessel Bx excluding the blood vessel information J in the ultrasound image U, and it is preferable that the highlight color is a color that is easily visible by the operator, such as yellow, orange, or light green.

The target blood vessel Bx in the ultrasound image U is highlighted in this way, whereby it is possible to allow the operator to easily recognize the position of the target blood vessel Bx in inserting the insert C into the target blood vessel Bx, and to improve the accuracy of the insertion operation of the insert C.

In the third embodiment, the apparatus controller 13 performs control such that the highlighting unit 10 and the blood vessel information display unit 17 set a color (that is, a background color) of the display region of the blood vessel information J and the highlight color in highlighting the target blood vessel Bx to the same color. With this, since the background color of the blood vessel information J and the target blood vessel Bx are displayed in the same color in the ultrasound image U, it is possible to allow the operator to easily recognize the blood vessel B that has information regarding the diameter and the depth indicated by the blood vessel information J. The effect is particularly effective, for example, in a situation in which the blood vessel B that has information regarding the diameter and the depth indicated by the blood vessel information J is hardly recognized since the blood vessel information J is displayed at a position far from the target blood vessel Bx.

EXPLANATION OF REFERENCES

1, 1A, 1B, 1C: ultrasound diagnostic apparatus
2: transducer array
3: transmission circuit
4: reception circuit
5: transmission and reception circuit
6: image generation unit
7: display controller
8: display device
10: highlighting unit
11: image acquisition unit
12: scene determination unit
13: apparatus controller
14: input device
15: storage unit
16: blood vessel information acquisition unit
17: blood vessel information display unit
18: region-of-interest detection unit
21: ultrasound probe
22: processor
23: amplification unit
24: AD conversion unit
25: beam former
26: signal processing unit
27: DSC
28: image processing unit
41: ultrasound diagnostic apparatus body B: blood vessel
Bx: target blood vessel
C: insert
d1: diameter
d2: depth
E: lesion portion
F: peripheral tissue
H: display range
J: blood vessel information
NW: network
U: ultrasound image

What is claimed is:

1. An ultrasound diagnostic apparatus that displays a blood vessel of a subject in an ultrasound image, the ultrasound diagnostic apparatus comprising:
   a transducer array;
   a processor; and
   a display device,
   wherein the processor is configured to:
      cause the transducer array to transmit an ultrasound beam toward the subject,
      receive an ultrasound echo by the subject to acquire an ultrasound image,
      display on the display device the ultrasound image,
      detect a target blood vessel in the ultrasound image and an insert puncturing the subject by analyzing the ultrasound image,
      determine at least one of presence or absence of the insert and the target blood vessel in the ultrasound image, a position of each of the target blood vessel and the insert in the ultrasound image, or an observation direction of the target blood vessel and the insert, by analyzing the ultrasound image,
      based on the at least one, determine a scene in a case where the ultrasound image is acquired,
      detect a region of interest to be noticed other than the target blood vessel in the ultrasound image, the region of interest corresponding to the determined scene,
      acquire blood vessel information including at least one of a diameter or a depth of the detected target blood vessel, and
      display the acquired blood vessel information within a display range of the ultrasound image in the display device, and
   wherein in a case where the target blood vessel is an entire blood vessel and the region of interest is detected, the processor is configured to decide a display region of the blood vessel information in the display range based on a position of the region of interest and to display the blood vessel information in the decided display region,
   in a case where the scene is a search scene where the target blood vessel is searched, the region of interest is a lesion portion inside the subject or a blood vessel other than the target blood vessel,
   in a case where the scene is an insertion scene where the insert punctures and is inserted toward the target blood vessel, the region of interest is at least one of a distal end of the insert or a tissue positioned near the distal end of the insert inside the subject, and
   in a case where the scene is a placement scene where a distal end part of the insert is within the target blood vessel, the region of interest is the distal end part of the insert or a lesion portion inside the subject.

2. The ultrasound diagnostic apparatus according to claim 1, wherein the processor extracts a display candidate region avoiding the target blood vessel and the region of interest within the display range and decides the display region from the extracted display candidate region.

3. The ultrasound diagnostic apparatus according to claim 2, wherein the processor decides the display region such that at least a part of the blood vessel information overlaps the region of interest in a case where the display candidate region is not extracted within the display range.

4. The ultrasound diagnostic apparatus according to claim 3, wherein, in a case where the processor detects a plurality of the regions of interest, the processor sets priority to each of the plurality of the regions of interest and decides the display region such that at least a part of the blood vessel information overlaps the region of interest with a lower priority selected from the plurality of the regions in a case where the display candidate region is not extracted within the display range.

5. The ultrasound diagnostic apparatus according to claim 4, wherein the processor sets the priority of each of the plurality of the regions of interest based on the position of each of the plurality of the regions of interest in the display range.

6. The ultrasound diagnostic apparatus according to claim 1, wherein, in a case where the determined scene is a search scene where the target blood vessel is searched, the processor detects a lesion portion inside the subject or a blood vessel other than the target blood vessel as the region of interest.

7. The ultrasound diagnostic apparatus according to claim 6, wherein a blood vessel into which an insert puncturing the subject is inserted, among blood vessels of the subject corresponds to the target blood vessel, and the processor determines that the scene is the search scene in a case where the blood vessel of the subject is detected in the ultrasound image and the insert is not detected by analyzing the ultrasound image.

8. The ultrasound diagnostic apparatus according to claim 6, wherein the processor continuously acquires the ultrasound images at a given frame rate, and the processor analyzes the ultrasound images of a plurality of frames continuously acquired and determines that the scene is the search scene in a case where appearance and disappearance of the blood vessel are repeated in the ultrasound images of the plurality of frames and in a case where a position of the blood vessel is changed in the ultrasound images of the plurality of frames.

9. The ultrasound diagnostic apparatus according to claim 1, wherein a blood vessel into which an insert puncturing the subject is inserted, among blood vessels of the subject corresponds to the target blood vessel, and in a case where the determined scene is an insertion scene where the insert punctures and is moving toward the target blood vessel, the processor detects at least one of a distal end of the insert or a tissue positioned near the distal end of the insert inside the subject as the region of interest.

10. The ultrasound diagnostic apparatus according to claim 9, wherein the insert is a catheter with a puncture needle, and the processor determines that the scene is the insertion scene in a case where the blood vessel of the subject and a distal end of the puncture needle are detected in the ultrasound image by analyzing the ultrasound image.

11. The ultrasound diagnostic apparatus according to claim 9, wherein the processor continuously acquires the ultrasound images at a given frame rate, and the processor analyzes the ultrasound images of a plurality of frames continuously acquired and determines that the scene is the insertion scene in a case where a position of the insert is changed to approach the target blood vessel in the ultrasound images of the plurality of frames and in a case where an observation direction of the blood vessel and the insert is switched in the ultrasound images of the plurality of frames.

12. The ultrasound diagnostic apparatus according to claim 1, wherein a blood vessel into which an insert puncturing the subject is inserted, among blood vessels of the subject corresponds to the target blood vessel, and in a case where the determined scene is a placement scene where a distal end part of the insert is placed inside the target blood vessel, the processor detects the distal end part of the insert or a lesion portion inside the subject as the region of interest.

13. The ultrasound diagnostic apparatus according to claim 12, wherein the insert is a catheter with a puncture needle, and the processor determines that the scene is the placement scene in a case where a distal end part of the catheter present inside the blood vessel in a state in which the puncture needle is no longer present inside the distal end part of the catheter is detected in the ultrasound image by analyzing the ultrasound image.

14. The ultrasound diagnostic apparatus according to claim 12, wherein the processor continuously acquires the ultrasound images at a given frame rate, and the processor analyzes the ultrasound images of a plurality of frames continuously acquired and determines that the scene is the placement scene in a case where appearance and disappearance of the distal end part of the insert are repeated in the ultrasound images of the plurality of frames and in a case where appearance and disappearance of the lesion portion inside the subject are repeated in the ultrasound images of the plurality of frames.

15. The ultrasound diagnostic apparatus according to claim 1, wherein, in a case where a plurality of the target blood vessels in the ultrasound image are detected, the processor acquires the blood vessel information on each of the plurality of the detected target blood vessels, the processor simultaneously displays the blood vessel information of each of the acquired plurality of the target blood vessels within the display range, and in a case where the region of interest is detected, the processor decides the display region for each target blood vessel based on the position of the region of interest such that the blood vessel information of each of the plurality of the target blood vessels is displayed separately.

16. The ultrasound diagnostic apparatus according to claim 1, wherein the processor detects the target blood vessel in the ultrasound image by analyzing the ultrasound image and fills the detected target blood vessel with a highlight color to highlight the target blood vessel, and the processor sets a color of the display region of the blood vessel information and the highlight color in highlighting the target blood vessel to the same color.

17. The ultrasound diagnostic apparatus according to claim 1, further comprising:

an ultrasound probe having the transducer array, wherein the ultrasound probe is connected to the processor, the ultrasound diagnostic apparatus includes a transmission circuit that causes the transducer array to transmit the ultrasound beam toward the subject, and a reception circuit that processes a signal output from the transducer array having received the ultrasound echo generated inside the subject to generate a sound ray signal, the processor generates the ultrasound image based on the sound ray signal generated by the reception circuit, and each of the transmission circuit and the reception circuit is provided in the ultrasound probe or the processor.

18. An ultrasound diagnostic apparatus that displays a blood vessel of a subject in an ultrasound image, the ultrasound diagnostic apparatus comprising:

a transducer array;

a processor; and a display device, wherein the processor is configured to:

cause the transducer array to transmit an ultrasound beam toward the subject, receive an ultrasound echo by the subject to acquire an ultrasound image, detect a blood vessel region including a target blood vessel in the ultrasound image, acquire blood vessel information including at least one of a diameter or a depth of the detected target blood vessel, further detect an insert in the ultrasound image, in a case where a distal end of the insert is detected to be within the target blood vessel, determine a display region excluding both the blood vessel region and the insert in the ultrasound image, and display the ultrasound image and the acquired blood vessel information within the display region in the display device.

19. The ultrasound diagnostic apparatus according to claim 18, wherein the processor is further configured to:

analyze the ultrasound image to determine whether a distal end of the insert is within the target blood vessel or out of the target blood vessel, further detect, in a case that the distal end is within the blood vessel, a lesion portion in the ultrasound image, and determine the display region excluding the blood vessel region, the insert and the lesion portion.

20. The ultrasound diagnostic apparatus according to claim 18, wherein, in a case where a plurality of the target blood vessels in the ultrasound image are detected, the processor acquires the blood vessel information on each of the plurality of the detected target blood vessels, the processor simultaneously displays the blood vessel information of each of the acquired plurality of the target blood vessels within a display range of the ultrasound image in the display device.

* * * * *